(12) United States Patent
Davies et al.

(10) Patent No.: US 12,161,390 B2
(45) Date of Patent: *Dec. 10, 2024

(54) CONNECTOR SYSTEM FOR ELECTROSURGICAL DEVICE

(71) Applicant: Boston Scientific Medical Device Limited, Galway (IE)

(72) Inventors: Gareth Davies, Toronto (CA); Mahmood Mirza, North York (CA)

(73) Assignee: Boston Scientific Medical Device Limited, Galway (IE)

( * ) Notice: Subject to any disclaimer, the term of this patent is extended or adjusted under 35 U.S.C. 154(b) by 1088 days.

This patent is subject to a terminal disclaimer.

(21) Appl. No.: 17/074,084

(22) Filed: Oct. 19, 2020

(65) Prior Publication Data

US 2021/0121227 A1 Apr. 29, 2021

Related U.S. Application Data

(60) Continuation-in-part of application No. 16/532,980, filed on Aug. 6, 2019, now Pat. No. 11,666,377,
(Continued)

(51) Int. Cl.
*A61B 18/12* (2006.01)
*A61B 18/14* (2006.01)
(Continued)

(52) U.S. Cl.
CPC . *A61B 18/1482* (2013.01); *A61B 2018/00011* (2013.01); *A61B 2018/00083* (2013.01);
(Continued)

(58) Field of Classification Search
CPC ......... A61B 18/14; A61B 18/00; A61B 18/18; A61B 90/00; A61B 18/1482;
(Continued)

(56) References Cited

U.S. PATENT DOCUMENTS

| 175,254 A | 3/1876 | Oberly |
| 827,626 A | 7/1906 | Gillet |

(Continued)

FOREIGN PATENT DOCUMENTS

| EP | 0192724 A1 | 9/1986 |
| EP | 0315730 A2 | 5/1989 |

(Continued)

OTHER PUBLICATIONS

N Shimko, P. Savard, K Shah. "Radio frequency perforation of cardiac tissue: modeling and experimental results". Med. Biol. Eng. Comput. 38:575-582 (2000).

(Continued)

*Primary Examiner* — Michael F Peffley
*Assistant Examiner* — Amanda L Zink
(74) *Attorney, Agent, or Firm* — Nelson Mullins Riley & Scarborough LLP

(57) ABSTRACT

An electrosurgical device for puncturing tissue comprises an electrically conductive elongate member which is capable of force transmission from a distal portion of the electrosurgical device to a proximal portion of the electrosurgical device to thereby provide tactile feedback to a user. The proximal portion comprises a connector system for connecting a source of energy and a source of fluid to an electrosurgical device. The connector system includes a hub which includes an electrically conductive lengthwise member having a lengthwise member distal region and a lengthwise member proximal region. The lengthwise member defines a hub lumen therebetween and is configured to be operatively coupled to an electrosurgical device.

20 Claims, 16 Drawing Sheets

Related U.S. Application Data which is a continuation-in-part of application No. 14/222,909, filed on Mar. 24, 2014, now Pat. No. 10,493,259, which is a continuation-in-part of application No. 13/468,939, filed on May 10, 2012, now Pat. No. 8,679,107, which is a division of application No. 11/905,447, filed on Oct. 1, 2007, now Pat. No. 8,192,425.

(60) Provisional application No. 60/884,285, filed on Jan. 10, 2007, provisional application No. 60/827,452, filed on Sep. 29, 2006.

(51) Int. Cl.
  *A61B 18/00* (2006.01)
  *A61B 90/00* (2016.01)

(52) U.S. Cl.
  CPC ............ *A61B 2018/00351* (2013.01); *A61B 2018/00839* (2013.01); *A61B 18/1492* (2013.01); *A61B 2090/064* (2016.02); *A61B 2218/002* (2013.01)

(58) Field of Classification Search
  CPC ...... A61B 18/1492; A61B 2018/00011; A61B 2018/00083; A61B 2018/00351; A61B 2018/00839; A61B 2090/064; A61B 2218/002

See application file for complete search history.

(56) References Cited

U.S. PATENT DOCUMENTS

| | | |
|---|---|---|
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A * | 4/1991 | Acker ............... A61B 18/082 606/32 |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Edwin |
| 5,281,216 A | 1/1994 | Klicek |
| 5,300,068 A | 4/1994 | Rosar et al. |
| 5,300,069 A | 4/1994 | Hunsberger et al. |
| 5,314,418 A * | 5/1994 | Takano ............... A61M 60/279 604/525 |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A * | 3/1996 | Swartz ............... A61M 25/0041 604/528 |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Arsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A * | 5/2000 | Saadat ............... A61B 18/14 607/101 |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |

(56) References Cited

U.S. PATENT DOCUMENTS

| | | |
|---|---|---|
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 * | 2/2001 | Wrublewski ....... A61B 18/1402 606/49 |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 * | 9/2001 | Makower ............... A61F 2/2493 606/198 |
| 6,292,678 B1 | 9/2001 | Hall et al. |
| 6,293,945 B1 * | 9/2001 | Parins ................. A61B 18/1402 606/49 |
| 6,296,615 B1 | 10/2001 | Brockway et al. |
| 6,296,636 B1 | 10/2001 | Cheng et al. |
| 6,302,898 B1 * | 10/2001 | Edwards ........... A61M 25/0662 606/213 |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 * | 5/2003 | Chandrasekaran ......................... A61B 18/1492 606/41 |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 * | 2/2008 | Sage ................. A61B 18/1492 606/41 |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 * | 3/2010 | Guerra ................... A61B 18/14 606/49 |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McLntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 * | 7/2004 | Uchida .............. A61B 17/1671 607/113 |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 * | 3/2005 | Hartley .............. A61B 18/1492 606/41 |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |

(56) References Cited

U.S. PATENT DOCUMENTS

| | | |
|---|---|---|
| 2006/0106375 A1 | 5/2006 | Werneth et al. |
| 2006/0135962 A1 | 6/2006 | Kick et al. |
| 2006/0142756 A1* | 6/2006 | Davies ............... A61B 18/1492 606/45 |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1* | 11/2006 | Ryan ............... A61B 17/32002 606/45 |
| 2006/0276710 A1 | 12/2006 | Krishnan |
| 2007/0060879 A1 | 3/2007 | Weitzner et al. |
| 2007/0066975 A1* | 3/2007 | Wong ..................... A61B 18/24 606/45 |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2019/0021763 A1 | 1/2019 | Zhou et al. |
| 2019/0247035 A1 | 8/2019 | Gittard et al. |

FOREIGN PATENT DOCUMENTS

| | | |
|---|---|---|
| EP | 1169976 A1 | 1/2002 |
| EP | 1474203 A2 | 11/2004 |
| EP | 1920724 A1 | 5/2008 |
| EP | 1943974 A1 | 7/2008 |
| GB | 2437058 A | 10/2007 |
| JP | 07-303703 A | 11/1995 |
| WO | 93/20747 A1 | 10/1993 |
| WO | 98/56324 A1 | 12/1998 |
| WO | 00/19917 A1 | 4/2000 |
| WO | 00/33909 A1 | 6/2000 |
| WO | 00/51511 A1 | 9/2000 |
| WO | 01/17600 A1 | 3/2001 |
| WO | 01/93939 A1 | 12/2001 |
| WO | 02/58780 A1 | 8/2002 |
| WO | 02/94334 A1 | 11/2002 |
| WO | 03/68311 A2 | 8/2003 |
| WO | 2004/026131 A1 | 4/2004 |
| WO | 2004/026134 A1 | 4/2004 |
| WO | 2004/039433 A2 | 5/2004 |
| WO | 2004/064657 A2 | 8/2004 |
| WO | 2005/046487 A1 | 5/2005 |
| WO | 2006/039531 A2 | 4/2006 |
| WO | 2007/082343 A1 | 7/2007 |
| WO | 2010/078151 A1 | 7/2010 |
| WO | 2013/101632 A1 | 7/2013 |
| WO | 2013/179103 A1 | 12/2013 |

OTHER PUBLICATIONS

Patent Cooperation Treaty, International Preliminary Report on Patentability, International Application No. PCT/IB2015/052118, dated Sep. 27, 2016.
Patent Cooperation Treaty, International Search Report for International Application No. PCT/IB2015/052118, dated Jun. 26, 2015.
Pressure Products, Inc. http://www.pressure-products.com/Downloads/Education.sub-.-PDFs/Using.sub-.-CSG.sub.-v2.pdf. 4 pages. 2005.
Shyam S. Kothari, Sanjeev K. Sharma, Nitish Naik; Radiofrequency Perforation for Pulmonary Atresia and Intact Ventricular Septum; Indian Heart J Jan.-Feb. 2004;56(1):50-3 (Actual publication after Feb. 2004).
Suhonen M. et al. Recanalization of arterial occlusions using a specially designed steering catheter. European Radiology: 2, 264-265(1992).
Supplementary European Search Report, EP 15 76 8911, search completed on Nov. 1, 2017.
Szili-Torok, T. et al. (2001) Transseptal Left Heart Catherisation Guided by Intracardiac Echocardiography, Heart 86:e11.
T Abdel-Massih, Y Boudjemline, P Bonhoeffer. "Unusual Interventional management in an adult with tetralogy of Fallot". Cardiol Young. 13(2):203-205 (Apr. 2003).
T Humpl, B Soderberg, BW McCrindle, DG Nykanen, RM Freedom, WG Williams, LN Benson. "Percutaneous Balloon Valvotomy in Pulmonary Atresia with Intact Ventricular Septum: Impact on Patient Care". Circulation. 108(7): 826-832 (Aug. 2003).
Timothy A.M. Chuter, "Branched and Fenestrated Stent Grafts for Endovascular Repair of Thoracic Aortic Aneurysms", Oct. 27, 2005, pp. 111A-115A, vol. 43, No. A, Publisher: The Society for Vascular Sugery, Published in: US.
Tsung O. Cheng. "All Roads Lead to Rome:Transjugular or Transfemoral Approach to Percutaneous Transseptal Balloon Mitral Valvuloplasty?". Catheterization and Cardiovascular Interventions 59:266-267 (2003).
Veldtman, Hartley, Visram, Benson. Radiofrequency Applications in Congenital Heart Disease. Expert Rev Cardiovaso Ther. Jan. 2004;2(1):117-26.
Abstract of European Patent No. 0315730 to Osypka. May 1989.
Abstract of Leonard W.H. Tse et al., "In Vivo Antegrade Fenestration of Abdominal Aortic Stent-Grafts", "Journal of Endovascular Therapy", Apr. 2007, pp. 158-167, vol. 14, No. 2, Publisher: Journal of Endovascular Therapy, Published in: US.
Abstract of Richard G. McWilliams et al., "In Situ Stent-Graft Fenestration to Preserve the Left Subclavian Artery", "Journal of Endovascular Therapy", Apr. 2004, pp. 170-174, vol. 11, No. 2, Publisher: Journal of Endovascular Therapy, Published in: US.
Abstract of Richard G. McWilliams et al., "Retrograde Fenestration of Endoluminal Grafts From Target Vessels: Feasibility, Technique, and Potential Usage", "Journal of Endovascular Therapy", Oct. 2003, pp. 946-952, vol. 10, No. 5, Publisher: Journal of Endovascular Therapy, Published in: US.
Benson, Lee N., David Nykanen, Amanda Collison, "Radiofrequency Perforation in the Treatment of Congenital Heart Disease". Catherizations and Cardiovascular Interventions; 56: 72-82, 2002.
Boston Scientific Corporation "http://www.bostonscientific.com/med.sub.-specialty/deviceDetail.jsp?tas-k=tskBasicDevice.jsp&sectionId=4&relId=2,74,75,76&deviceId=11026&uniqueID=-MPDB2799". PT2 Guide Wire. 2 pages (Date of printing—Jun. 2005).
Boston Scientific Corporation. "http://www.bostonscientific.com/med.sub.--specialty/deviceDetail.jsp?tas-k=tskBasicDevice.jsp

(56) References Cited

OTHER PUBLICATIONS

&sectionid=4&relId=1,20,21,22&deviceid=488&uniqueID=MP-DB58". Explorer ST Catheters. 2 pages. (Date or printing—Jun. 2005).

Brendan M. Stanley et al., "Fenestration in Endovascular Grafts for Aortic Aneurysm Repair: New Horizons for Preserving Blood Flow in Branch Vessels", "Journal of Endovascular Therapy", Feb. 2001, pp. 16-24, vol. 8, Publisher: Journal of Endovascular Therapy, Published in: US.

C.R. Conti. "Transseptal Left Heart Catheterization for Radiofrequency Ablation of Accessory Pathways". Clin. Cardiel. 16, 367-368 (1993).

CA Pedra, LN De Sousa, SR Pedra, WP Ferreira, SL Braga, CA Esteves, MV Santant, JE Sousa, VF Fontes. "New Percutaneous Techniques for Perforating the Pulmonary Valve in Pulmonary Atresia with Intact Ventricular Septum". Arq. Bras Cariol. 77(5):471-478 (2001).

CA Pedra, LN de Sousa, SR Pedra, WP Ferreira, SL Braga, CA Esteves, MV Santant, JE Sousa, VF Fontes. "New Percutaneous Techniques for Perforating the Pulmonary Valve in Pulmonary Atresia with Intact Ventricular Septum". Arq. Bras Cariol. 77(5):479-486 Nov. 2001.

CA Pedra, RM Filho, RS Arrieta, R Tellez, VF Fontes. "Recanalizationof a discrete atretic right pulmonary artery segment with a new radiofrequency system". Catheter Cardiovasc. Interv. 60(1):82-87 (Sep. 2003).

Christodoulos Stefanadis. "Retrograde Nontransseptal Balloon Mitral Valvuloplasty: Immediate Results and Intermediate Long-Term Outcome in 441 Cases—A Multicentre Experience". Journal of the American College of Cardiology. 32(4): 1009-16 (1998).

Christophe Fink, Mattias Peuster, Harald Bertram, Gerd Hausdorf; Transcatheter Recanalization of the Left Main Pulmonary Artery After Four Years of Complete Occlusion; Catheterization and Cardiovascular Interventions Jan. 2004;2(1):117-26.

Conti "finite element analysis of self-expanding braided wirestent" 2006-2007.

Conti C. R., "Transseptal Left Heart Catheterization for Radiofrequency Ablation of Accessory Pathways". Clinical Cardiology; 16: 367-368, 1993.

Daniel S. Levi, Juan C. Alejos, John W. Moore; Future of Interventional Cardiology in Pediatrics; Current Opinion in Cardiology Mar. 2003;18(2):79-90.

DG Nykanen, J Phikala, GP Taylor, LN Benson. "Radiofrequency assisted perforation of the atrial septum in a swine model: feasibility, biophysical and histological characteristics", Circulation. 100(Suppl 1):1-804 (1999).

Edward B. Diethrich, "Side Branch Preservation During Endovascular Aortic Aneurysm Repair", "Journal of Endovascular Therapy", Feb. 2001, pp. 1-2, vol. 8, Publisher: Journal of Endovascular Therapy, Published in: US.

F Godart, C Francart, GM Breviere, C Rey. "Pulmonary vavulotomy with the Nykanen radiofrequency guide in pulmonary atresia with intact interventricular septum", Arch Mal Coeur Vaiss. 96(5):517-520 (May 2003), Article is in French with an English summary.

Fink, Peuster, Bertram, Hausdorf. Transcatheter Recanalization of the Left Main Pulmonary Artery after Four Years of Complete Occlusion. Catheterization and Cardiovascular Interventions. May 2001;53(1):81-4.

First Office Action for Chinese Application, Application/Patent No. 2015800262435, Issue Serial No. 2018122001954460, dated Dec. 25, 2018.

Frank R. Arko III, "In Pursuit of an Off-the Shelf Fenestrated Stent-Graft: Radiofrequency Perforation for In Vivo Antegrade Fenestration", "Journal of Endovascular Therapy", Apr. 2010, pp. 199-200, vol. 17, No. 2, Publisher: Journal of Endovascular Therapy, Published in: US.

G Hausdorf, I Schulze-Neick, PE Lange; Radiofrequency-assisted "reconstruction" of the Right Ventricular Outflow Tract in Muscular Pulmonary Atresia with Ventricular Septal Defect; British Heart Journal, Apr. 1993.69(4):343-6.

G Veldtman, A Peirone, LN Benson. "Radiofrequency perforation of the atrial septum: Preliminary experimental evaluation and development." PICS VII Abstracts. Catheter Cardiovasc Interv. 60(1):132 (Sep. 2003).

George Joseph, Dibya K. Baruah, Sajy V. Kuruttukulam, Sunil Thomas Chandy, Shanker Krishnaswami. "Transjugular Approach to Transseptal Balloon Mitral Valvuloplasty". Catheterization and Cardiovascular Diagnosis 42:219-226 (1997).

George Joseph, G. Rajendiran, K. Abhaichand Rajpal. "Transjugular Approach to Concurrent Mitral-Aortic and Mitral-Tricuspid Balloon Valvuloplasty". Catheterization and Cardiovascular Interventions 49:335-341 (2000).

George Joseph, K.P. Suresh Kumar, Paul V. George, Subodh Dhanawade. "Right Internal Jugular Vein Approach as an Alternative in Balloon Pulmonary Valvuloplasty". Catheterization and Cardiovascular Interventions 46:425-429 (1999).

George Joseph, Oommen K. George, Asishkumar Mandalay, Sunil Sathe. "Transjugular Approach to Balloon Mitral Valvuloplasty Helps Overcome Impediments Caused by Anatomical Alterations". Catheterization and Cardiovascular Interventions 57:353-362 (2002).

Gero Hausdorf, Martin Schneider. Peter Lange; Catheter Creation of an Open Outflow Tract in Previously Atretic Right Ventricular Outflow Tract Associated with Ventricular Septal Defect; The American Journal of Cardiology, Aug. 1, 1993;72(3):354-6.

Gideon J. Du Marchie Sarvaas, Kalyani R. Trivedi, Lisa K. Hornberger, K. Jin Lee, Hoel A. Kirsh, Lee N. Benson. "Radiofrequency-Assisted Atrial Septoplasty for an Intact Atrial Septum in Complex Congenital Heart Disease". Catheterization and Cardiovascular Interventions; 56: 412-415 (2002).

H Justino, LN Benson, DG Nykanen. "Transcatheter Creation of an Atrial Septal Defect Using Radiofrequency Perforation". Catheter Cardiovasc Interv. 54(1):83-87 (Sep. 2001).

Hector Biddogia, Juan P. Maciel, Jose A. Alvarez et al. "Transseptal Left Heart Catheterization: Usefulness of the Intracavitary Electrocardiogram in the Localization of the Fossa ovalis". Catheterization and Cardiovascular Diagnosis 24: 221-225 (1991).

Holzer, Hardin, Hill, Chisolm, Cheatham. Radiofrequency Energy—A Multi-Facetted Tool for the Congenital Interventionist. Congenital Cardiology Today. Jun. 2006; 4(6): 1.

Hugh Calkins, Yoon-Nyun Kim, Steve Schmaltz, Joao Sousa, Rafel El-Atassi, Angel Leon, Alan Kadish, Jonathan J. Langberg, Fred Morady; Electrogram Criteria for Identification of Appropriate Target Sites for Radiofrequency Catheter Ablation of Accessory Atrioventricular Connections; Feb. 1992;85(2):565-73.

International Search Report and Written Opinion received for PCT Patent Application No. PCT/US2007/061203, mailed on Oct. 26, 2007, 8 pages.

IntraLuminal Therapeutics, Inc. "http://www.intraluminal.com/products/catheter.html". Safe Cross Support Catheter. 1 page. (Date of Printing—Jun. 2005).

J. E Della, "Notice of Allowance in the case of U.S. Appl. No. 11/520,754", Jul. 2, 2010.

J. Thompson Sullebarger, Humberto Coto, Enrique Lopez, Dany Sayad, Hector L. Fontanet. "Transjugular Percutaneous Inoue Balloon Mitral Commissurotomy in a Patient With Inferior Vena Cava Obstruction After Liver Transplantation". Catheterization and Cardiovascular Interventions 59:261-265 (2003).

John Lennon Anderson et al., "Endoluminal Aortic Grafting with Renal and Superior Mesenteric Artery Incorporation by Graft Fenestration", "Journal of Endovascular Therapy", Feb. 2001, pp. 3-15, No. 8, Publisher: Journal of Endovascular Therapy, Published in: US.

Johnson & Johnson Gateway, LLC. "http://www.jnjgateway.com/home_jhtml;jsessionid=JNSFHTWOAOICOCQPCCECPJYK-B2IIWNSC?icc=USENG&page=viewContent&contentid=IC0de00100000524&nodekey=/Pr-od.sub.--Info/Specialty/Cardiovascular.sub.-and.sub.-Thoracic/Cardiac.su-b.-Diagnosis.sub.--Interventions/Diagnostic.sub.-Wires&.sub.--requestid =-228905", Diagnostic Guidewires, 4 pages.

Johnson & Johnson Gateway, LLC. "http://www.jnjgateway.com/home.jhtml?loc=USENG&page=viewContent&contentId=Ic0de00100001435&nodekey=/Prod.sub.-info/Spec-ialty/Arrhythmia.

(56) References Cited

OTHER PUBLICATIONS sub.--Management/Electrophysiology/EP.sub.-Diagnostic.su-b.-Catheters". EP Diagnostic Catheters, 2 pages (Date of printing—Jun. 2005).

Justino, Henri, Lee N. Benson, David G. Nykanen. "Transcatheter Creation of an Atrial Septal Defect Using Radiofrequency Perforation". Catheterization and Cardiovascular Interventions. 56: 412-415 (2002).

Kamal K. Sethi, Jagdish C. Mohan. "Editiorial Comment: Transseptal Catheterization for the Electrophysiologist: Modification with a 'View'". Journal of Interventional Cardian Physiology. 5, 97-99, 2001.

Kamal K. Sethi, Jagdish C. Mohan. "Editorial Comment: Transseptal Catheterization for the Electrophysiologist: Modification with a 'View'". Journal of Interventional Cardiac Physiology. 5, 97-99, 2001.

Lake Region Manufacturing, Inc. "http://www.lakergn.com/jmc.htm". Paragon Guidewire. 2 pages (Date of Printing—Jun. 2005).

Leonard W. H. Tse et al., "Radiofrequency Perforation System for an In Vivo Antegrade Fenestration of Aortic Stent-Grafts", "Journal of Endovascular Therapy", Apr. 2010, pp. 192-198, vol. 17, No. 2, Publisher: Journal of Endovascular Therapy, Published in: US.

Lepage, Lewis, Ruiz, Yamanishi, Padron, Hood. Angiopyroplasty using Electromagnetically Induced Focused Heat. Angiology. Jul. 1987;38(7):520-3.

M. F Peffley, "Notice of Allowance in the case of U.S. Appl. No. 10/666,301", Dec. 23, 2005.

Medtronic Inc. "http://www.medtronic.com/epsystems/diagnostic.sub.-catheters.html". Diagnostic Catheters. 7 pages (Date of Printing—Apr. 2005).

\* cited by examiner

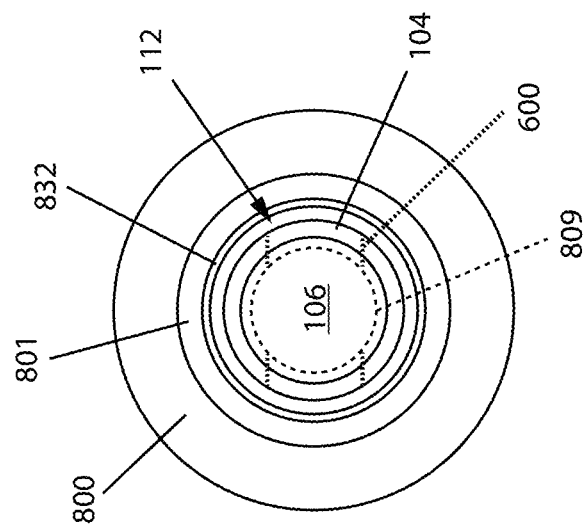
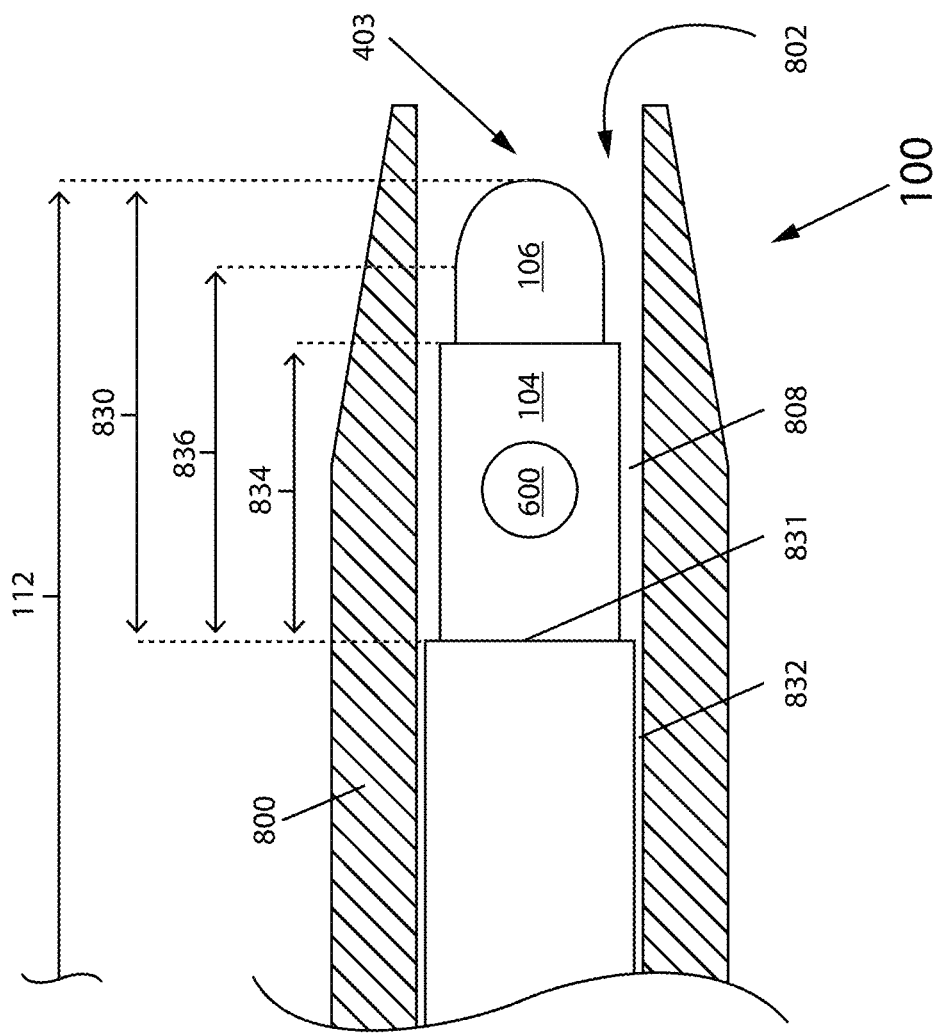

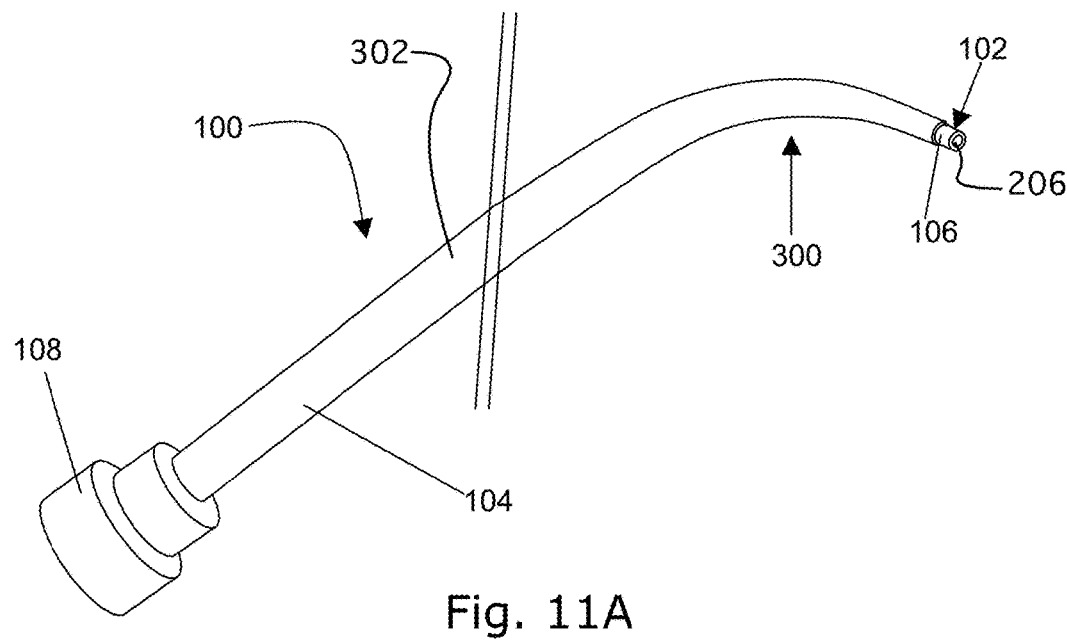
Fig. 11A
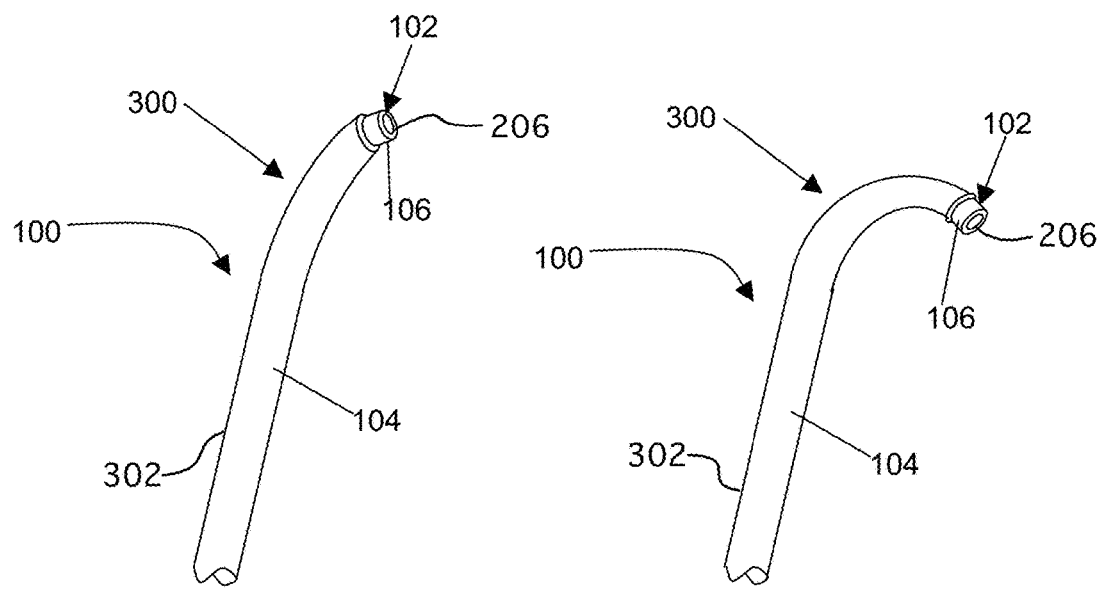
Fig. 11B
Fig. 11C

CONNECTOR SYSTEM FOR ELECTROSURGICAL DEVICE

CROSS-REFERENCES TO RELATED APPLICATIONS

This application is a continuation-in-part of U.S. application Ser. No. 16/532,980, filed on Aug. 6, 2019, now U.S. Pat. No. 11,666,377, which is a continuation-in-part of U.S. application Ser. No. 14/222,909, filed Mar. 24, 2014, now U.S. Pat. No. 10,493,259, which is a continuation-in-part of U.S. application Ser. No. 13/468,939, filed on May 10, 2012, now U.S. Pat. No. 8,679,107, which is a divisional application of, and claims priority from, U.S. application Ser. No. 11/905,447, filed on Oct. 1, 2007, now U.S. Pat. No. 8,192,425, which claims the benefit of: U.S. provisional application No. 60/827,452, filed on Sep. 29, 2006, and U.S. provisional application No. 60/884,285, filed on Jan. 10, 2007, all of which are incorporated by reference herein in their entirety.

FIELD OF THE INVENTION

The present invention relates generally to devices usable within the body of a patient to deliver energy to tissue. More specifically, the present invention is concerned to a connector system for connecting a source of energy and a source of fluid to an electrosurgical device.

SUMMARY OF THE DISCLOSURE

Mechanical force is typically used with a conventional transseptal needles to create a puncture. Under certain circumstances, however, mechanical force is not always effective at puncturing tissue. In such cases a physician may use electrical energy to create a puncture while having sufficient stiffness in the puncture device to provide tactile feedback, i.e. to use an electrosurgical device which is stiff. These requirements could be met by an electrosurgical device comprising an electrically conductive elongate member which is capable of force transmission from a distal portion of the electrosurgical device to a proximal portion of the electrosurgical device to thereby provide tactile feedback to a user, wherein the proximal portion comprises a connector systems having a hub. The hub comprises an electrically conductive lengthwise member having a lengthwise member distal region and a lengthwise member proximal region, wherein the lengthwise member defines a hub lumen therebetween for providing a conduit for flow of a fluid, said lengthwise member configured to be operatively coupled to an electrosurgical device. The hub further includes a hub fluid connector associated with the lengthwise member for operatively connecting the lengthwise member to a fluid source, and a hub electrical connector associated with the lengthwise member for electrically coupling the lengthwise member to an energy source. In use, the hub both conducts electricity and provides a conduit for fluid delivery. The hub is configured to be releasable such that it may be removable from the electrosurgical device or rotatable with respect to electrosurgical device.

In a first broad aspect, embodiments of the present invention comprise an electrosurgical device having an electrically conductive elongate member, wherein the device defines a proximal portion and a distal portion, with the electrically conductive elongate member being capable of force transmission from the distal portion to the proximal portion to thereby provide tactile feedback to a user. The proximal portion comprises a handle, with the handle including an electrical connector which is configured to receive, in a releasable manner, an electrically conductive component operable to be electrically coupled to an energy source.

As features of the first broad aspect: some embodiments have a distal tip including an electrode for delivering energy to a tissue; some embodiments include the handle having insulation for electrically insulating a user from the electrically conductive elongate member; some embodiments include the handle having ridges for enhancing grip and tactile feedback; some embodiments include the electrically conductive elongate member defining a lumen and the handle having a fluid connector for connecting the lumen to a source of fluid, with some of said embodiments having a distal end of the electrically conductive elongate member defining a distal aperture which is in fluid communication with the lumen.

As a feature of the first broad aspect, some embodiments comprise the electrical connector being electrically coupled to the electrically conductive elongate member, in some examples, through the handle. Some embodiments of this feature include the handle comprising a conductor such as conductive wire or conductive rigid member for electrically coupling the electrical connector to the electrically conductive elongate member.

As another feature of the first broad aspect, in some embodiments the electrical connector comprises a jack for receiving the electrically conductive component. Some of said embodiments further comprise a conductive wire extending from the handle to the jack, wherein the jack is electrically connected to an end of the wire such that the conductive wire electrically couples the jack to the handle.

Some embodiments of the first broad aspect include a force transmitting portion which extends between a distal portion of the electrosurgical device and a proximal portion of the electrosurgical device. In some of these embodiments, the force transmitting portion has a flexural rigidity of at least about 0.016 Nm2.

As a feature of the first broad aspect, some embodiments of the handle comprise a hub. Some embodiments having this feature comprise a distal tip which includes an electrode for delivering energy to a tissue. In some embodiments, the hub comprises electrical insulation for insulating a user from the electrically conductive elongate member. In some embodiments having this feature, the hub comprises ridges for enhancing grip and tactile feedback. In some examples, the electrically conductive elongate member defines a lumen, and the hub includes a fluid connector for connecting the lumen to a source of fluid. Some such examples include a distal end of the electrically conductive elongate member defining a distal aperture which is in fluid communication with the lumen. Some embodiments include the electrical connector being electrically coupled to the electrically conductive elongate member, with some such embodiments further comprising a conductive wire for electrically coupling the electrical connector to the electrically conductive elongate member.

In some embodiments wherein the handle comprises a hub, the electrical connector comprises a jack for receiving the electrically conductive component, with some such embodiments further comprising a conductive wire extending from the hub and the jack being electrically connected to a distal end of the wire such that the conductive wire electrically couples the jack to the hub. Some embodiments of this feature include a force transmitting portion which extends between a distal portion of the electrosurgical device and a proximal portion of the electrosurgical device. In some such embodiments, the force transmitting portion has a flexural rigidity of at least about 0.016 Nm2.

In one broad aspect, a connector system for connecting a source of energy and a source of fluid to an electrosurgical device is provided. The connector system comprises a hub. The hub comprises an electrically conductive lengthwise member having a lengthwise member distal region and a lengthwise member proximal region, wherein the lengthwise member (elongate member) defines a hub lumen therebetween for providing a conduit for flow of a fluid. The lengthwise member distal region is preferably structured to be operatively coupled to an electrosurgical device. Some embodiments of this aspect include a hub fluid connector associated with the lengthwise member for operatively connecting the lengthwise member to a fluid source and a hub electrical connector associated with the lengthwise member for electrically coupling the lengthwise member to an energy source. In a further embodiment, an electrically insulative material may be disposed on an inner wall of the lengthwise member in order to prevent energy from being conducted from the lengthwise member to a fluid within the hub lumen defined by the lengthwise member. In use, an electrical conduction pathway between the energy source and the electrosurgical device includes the lengthwise member, and whereby the lengthwise member provides a fluid pathway conduit between the fluid source and the electrosurgical device. Some embodiments of this broad aspect include wherein the hub is structured (or configured) to be removable from the electrosurgical device, thereby allowing other devices to be slid over the electrosurgical device, or wherein the hub is rotatable with respect to the electrosurgical device while maintaining electrical and fluid communication with the electrosurgical device. In such procedures, the hub may be locked or coupled to the electrosurgical device using a coupling mechanism during a portion of the procedure, preventing undesired disengagement and/or rotation of the hub from the electrosurgical device.

In a second broad aspect, embodiments of the present invention include a transseptal puncturing device comprising an electrically conductive elongate member and an electrode at a distal end of the electrically conductive elongate member for delivering energy to tissue, the transseptal puncturing device further including an electrical connector configured to receive, in a releasable manner, an electrically conductive component operable to be electrically coupled to an energy source.

As a feature of the second broad aspect, some embodiments include the electrically conductive elongate member defining a lumen and the transseptal puncturing device further comprising a handle which includes a fluid connector for connecting the lumen to a source of fluid. Some such embodiments include a distal portion of the transseptal puncturing device defining a distal aperture in fluid communication with the lumen.

Some embodiments of the second broad aspect include the transseptal puncturing device having an electrical insulation extending proximally from the electrode. Some embodiments include a distal tip of the transseptal puncturing device being substantially atraumatic. Some examples of the second broad aspect further comprise a handle having electrical insulation for insulating a user from the electrically conductive elongate member. In some such examples, the handle comprises ridges for enhancing tactile feedback.

Some embodiments of the second broad aspect include the electrical connector being electrically coupled to the electrically conductive elongate member. Some such embodiments further comprise a conductive wire for electrically coupling the electrical connector to the electrically conductive elongate member. In some examples of the second broad aspect, the electrical connector comprises a jack for receiving the electrically conductive component.

In a third broad aspect, embodiments of the present invention are for a method of using a transseptal puncturing device comprising an elongate member which is electrically conductive, an electrical connector in electrical communication with the elongate member, and an electrode at a distal end of the elongate member for delivering energy to tissue, the method comprising the steps of (1) connecting an electrically conductive component, which is in electrical communication with a source of energy, to the electrical connector, and (2) delivering electrical energy through the electrode to a tissue.

As a feature of the third broad aspect, some embodiments further comprise a step (3) of disconnecting the electrically conductive component from the electrical connector i.e. the electrically conductive component is releasably connected to the electrical connector.

In a fourth broad aspect, embodiments of the present invention include an electrosurgical device comprising an electrically conductive elongate member, with the device defining a proximal portion and a distal portion. The electrically conductive elongate member is capable of force transmission from the distal portion to the proximal portion to thereby provide tactile feedback to a user. The proximal portion comprises a handle, the handle having a connector means for receiving, in a releasable manner, an electrically conductive component, wherein the electrically conductive component is operable to be electrically coupled to an energy source.

BRIEF DESCRIPTION OF THE DRAWINGS

In order that the invention may be readily understood, embodiments of the invention are illustrated by way of examples in the accompanying drawings.

FIGS. 4A and 4B illustrate a partially cut-away side view and an end view, respectively, of a medical device and a tubular member in accordance with an embodiment of the present invention;

FIG. 11A illustrates a perspective view of a medical device in accordance with an yet another alternative embodiment of the present invention, the medical device including a curved section;

FIG. 11B illustrates a partial perspective view of a medical device in accordance with yet another alternative embodiment of the present invention, the medical device including an alternative curved section;

FIG. 11C illustrates a partial perspective view of a medical device in accordance with yet another alternative embodiment of the present invention, the medical device including another alternative curved section;

DETAILED DESCRIPTION

Figure 1:
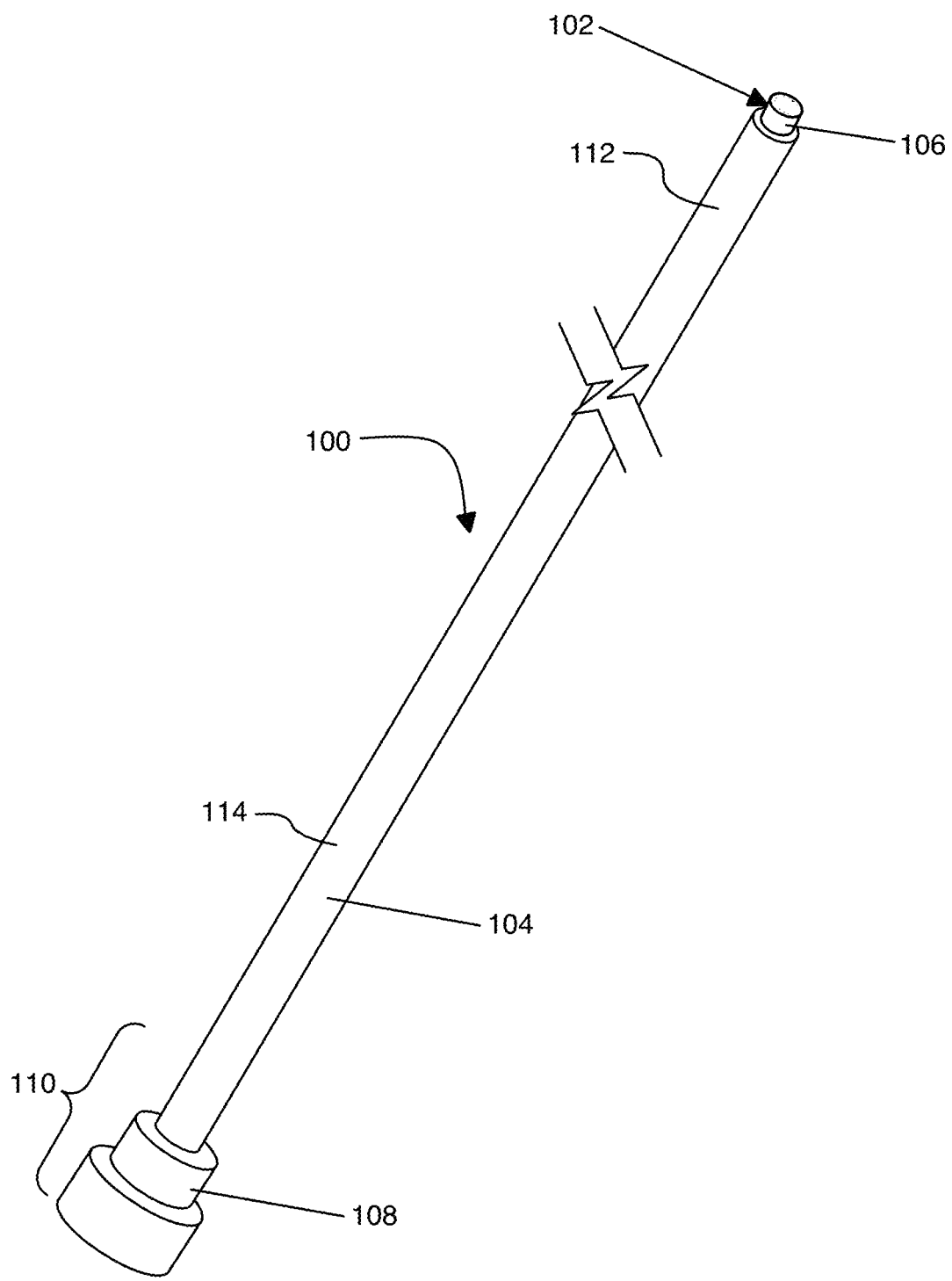
FIG. 1 illustrates a perspective view of a medical device in accordance with an embodiment of the present invention.

Devices used for puncturing tissue, such as the septal tissue of a patient's heart, are typically either mechanical or electrosurgical in nature. Usually, such devices are inserted into a patient's body through tubular devices such as dilators or sheaths. Mechanical force is normally used with a conventional Brockenbrough transseptal needle to create a puncture. A Brockenbrough needle has a sharp beveled tip and a forward-facing aperture that may be used for injecting fluid or monitoring pressure. Under certain circumstances, however, mechanical force is not always effective at puncturing tissue. In such cases, physicians have proposed using an electrocautery generator or the like to electrify the mechanical needle and thereby produce an ad hoc electrosurgical device with a forward facing aperture. One drawback to electrifying a non-insulated Brockenbrough needle is a risk of burns to the patient and physician. While a dilator or sheath provides some insulation for the part of the non-insulated Brockenbrough needle contained therein, there is still potential for burns to the patient and physician by sections of the needle outside of the dilator or sheath. Also, any fluids (e.g. blood, cooling water) inside of the dilator or sheath will be exposed to electricity such that the fluid may conduct electricity to outside of the dilator or sheath. Furthermore, there is a risk of tissue coring. A core (or plug) of tissue is typically cut from the tissue inside the ring-shaped distal tip of the needle upon delivery of energy. This tissue core is subsequently captured in the lumen of the electrosurgical device upon advancement of the needle through tissue. The tissue core may be released from the lumen, potentially leading to emboli and increasing the risk of a stroke or other ischemic event.

The present inventors have conceived of, and reduced to practice embodiments of an electrosurgical device configured for force transmission from a distal portion of the electrosurgical device to a proximal portion of the electrosurgical device to thereby provide tactile feedback to a user. The proximal portion of the device comprises a a hub, with the hub including an electrical connector which is configured to receive, in a releasable manner, an electrically conductive component which is operable to be in electrical communication with an energy source to allow the physician or other user to puncture a tissue layer, such as a septum. In some cases, a radiofrequency (RF) energy source is used to selectively apply RF energy to tissue. Typical embodiments of the device include insulation to protect the user and the patient, and are configured to avoid creating emboli. Some embodiments comprise a transseptal puncturing device having an electrically conductive elongate member and an electrode at a distal end of the electrically conductive elongate member for delivering energy to tissue, with the transseptal puncturing device further including an electrical connector configured to releasably receive, the electrically conductive component which is electrically coupled to an energy source.

With specific reference now to the drawings in detail, it is stressed that the particulars shown are by way of example and for purposes of illustrative discussion of embodiments of the present invention only. In this regard, no attempt is made to show structural details of the invention in more detail than is necessary for a fundamental understanding of the invention. The description taken with the drawings will make apparent to those skilled in the art how the several aspects of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As used herein, the terms 'proximal' and 'distal' are defined with respect to the user. That is, the term 'proximal' refers to a part or portion closer to the user, and the term 'distal' refers to a part or portion further away from the user when the device is in use. Also, it should be noted that while, for clarity of explanation, the term tubular or tubular member is used to describe the members that enclose the disclosed medical devices, the term tubular member is intended to describe both circular and non-circular embodiments of the enclosing member. The term tubular member is used in this disclosure to describe dilators, sheaths, and other members that define a lumen for containing a medical device.

Referring to FIG. 1, there is shown a medical device 100 in accordance with an embodiment of the present invention. The medical device 100 is usable for creating a channel at a target location in a body of a patient. The medical device 100 includes a handle 110, a distal portion 112 and a force transmitting portion 114 extending between the distal portion 112 and the handle 110. The distal portion 112 defines a distal portion length, and includes an electrode 106 and an electrical insulation 104 extending proximally from the electrode 106.

The force transmitting portion 114 defines a force transmitting portion length, the force transmitting portion length being larger than the distal portion length. In some embodiments of the invention, the force transmitting portion 114 has a force transmitting portion flexural rigidity of at least about 0.016 Nm2, for example about 0.017 Nm2. The force transmitting portion 114 has a force transmitting portion flexural rigidity allowing the transmission to the handle 110 of contact forces exerted on the distal portion 112 when the distal portion 112 contacts the target location to provide tactile feedback to the intended user. In addition, the force transmitting portion flexural rigidity allows for the transmission of force from the handle 110 to the distal portion 112 in order to, for example, advance the distal portion 112 within the body of the patient or to orient the distal portion 112 by applying torque to the handle 110.

Therefore, the proposed medical device 100 is structured such that it provides the intended user with a similar, or better, 'feel' as some prior art devices. That is, although the structure and function of the medical device 100 differs significantly from prior art devices.

In some embodiments of the invention, the distal portion 112 has a distal portion flexural rigidity of at least about 0.0019 Nm2, for example 0.0021 Nm2. Such values of flexural rigidity enhance the cognitive ergonomics of the proposed medical device 100 by providing tactile feedback to the intended user and allowing for the transmission of radial (torque) and longitudinal forces from the handle to the distal portion.

In typical embodiments of the invention, the medical device 100 includes an electrically conductive elongate member 102 having an electrical insulation 104 disposed thereon. The electrical insulation 104 substantially covers the entire outer surface of the elongate member 102 such that elongate member 102 is able to deliver energy from its proximal region to the electrode 106 at its distal region, without substantial leakage of energy along the length of the elongate member 102. The elongate member 102 defines a lumen 208 and at least one side-port 600 (shown, for example, in FIGS. 2A to 2D), which is in fluid communication with the lumen 208.

The one or more side-ports 600 are particularly useful in typical embodiments of medical device 100 wherein a lumen 208 of the elongate member 102 is not open to the surrounding environment via the distal end of the medical device 100 (i.e. wherein medical device 100 is a close-ended device), for example, in the embodiments of FIGS. 2A to 2E. In such embodiments, the lumen extends substantially longitudinally through the force transmitting portion 114 (FIG. 1), and through a section of the distal portion 112, and terminates in the distal portion 112 at a location substantially spaced apart from the distal tip 403, such that the distal tip 403 remains closed.

In embodiments comprising side-port(s) 600, the side-port(s) 600 allow for fluids to be injected into the surrounding environment from the lumen 208, and/or allow for pressure to be measured by providing a pressure transmitting lumen through medical device 100. In some examples, the side-port(s) 600 are formed radially through elongate member 102 and electrical insulation 104, thereby allowing for fluid communication between the surrounding environment and the lumen 208. In alternative embodiments, a side-port 600 is formed radially through a portion of the electrode 106.

Figure 2A:
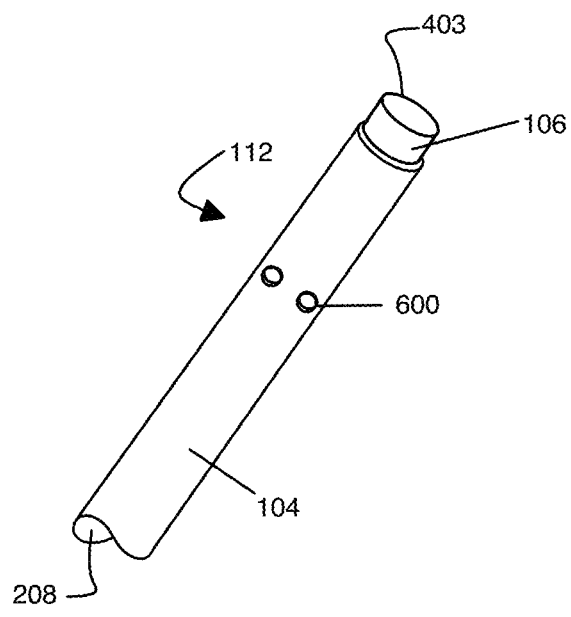
FIGS. 2A to 2D illustrate partial perspective views of distal regions of embodiments of medical devices.
Figure 2B:
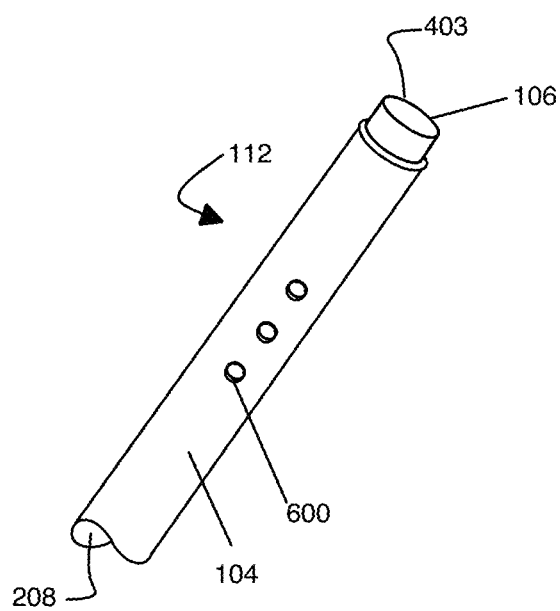
Figure 2C:
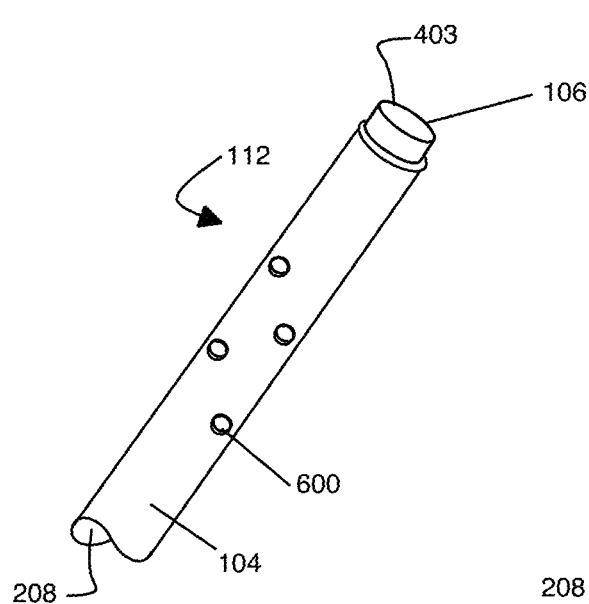
Figure 2D:
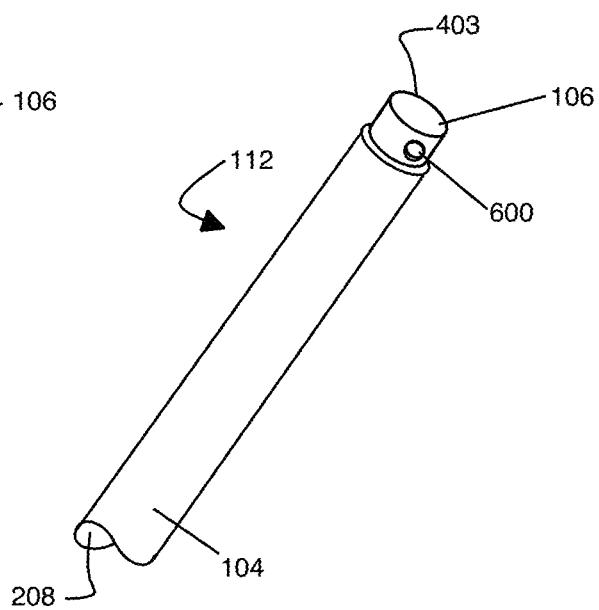

The size and shape of the side-port(s) 600 may vary depending on the intended application of the medical device 100, and the invention is not limited in this regard. For example, in one embodiment, the side-port(s) 600 is between about 0.25 mm and about 0.45 mm in diameter. Some embodiments include side-ports of more than one size. In addition, the number of side-ports 600 may vary, and they may be located anywhere along the medical device 100 that does not interfere with the functioning of the device. For example, as shown in FIG. 2A, the medical device 100 includes two side-ports 600 located about 1 cm from the distal end of the elongate member 102, at substantially the same longitudinal position along the elongate member 102. In another embodiment, as shown in FIG. 2B, the medical device 100 includes about 3 side-ports located at the same circumferential position and spaced longitudinally at about 1.0 cm, 1.5 cm, and 2.0 cm from the distal end of the elongate member 102. In another embodiment, as shown in FIG. 2C, the side-ports 600 are staggered, such that they are spaced apart both circumferentially as well as longitudinally. In a further embodiment, as shown in FIG. 2D, the side-ports 600 are located on the electrode 106. In some embodiments, the side-port(s) 600 have a smooth or rounded wall, which serves to minimize or reduce trauma to bodily tissue. For example, some such embodiments comprise one or more side-port(s) 600 with a smooth outer circumferential edge created by sanding the circumferential edges to a smooth finish or, for example, by coating the edges with a lubricious material.

When a medical device that relies on side-ports to provide fluid communication between its lumen and the surrounding environment is inside a lumen of a close-fitting member, the side-ports may be partially or completely occluded or blocked. The embodiments of FIGS. 4 to 9 relate to an apparatus that provides an effective conduit from the lumen of medical device to the environment outside of the device, and methods of using such apparatus.

Figure 2E:
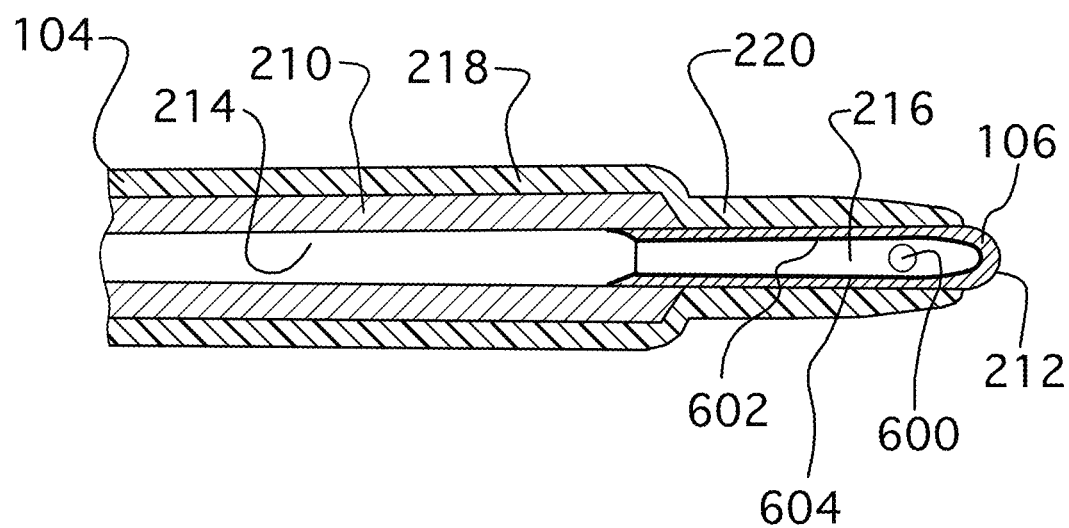
FIG. 2E illustrates a cross-sectional view of a distal region of an embodiment of a medical device.

FIGS. 4A and 4B illustrate a partially cut-away side view and an end view, respectively, of a distal portion 112 of medical device 100 positioned within tubular member 800. As described in more detail herein below, some embodiments of medical device 100 are comprised of a single piece elongate member 102 (as shown in FIG. 1 and FIG. 10A) and some other embodiments of medical device 100 are comprised of two elongate members, main member 210 and end member 212, which are joined together (as shown in FIGS. 10D and 2E). Depending on the embodiment of medical device 100 being considered, distal portion 112 may be the distal portion of a single piece elongate member 102, the distal portion of an end member 212, or the distal portion of some other embodiment of medical device 100. In FIGS. 4 to 9, the lumen defined by distal portion 112 may be either lumen 208 of elongate member 102 or end member lumen 216. For descriptive purposes, the lumen defined by distal portion 112 in FIGS. 4 to 9 is referred to as device lumen 809.

Tubular member 800 may comprise a dilator, a sheath, or some other member defining a lumen configured to receive a medical device 100.

Referring to FIGS. 4A and 4B, illustrated features of an embodiment of distal portion 112 of medical device 100 include a change in diameter 831, a distal portion 830, device lumen 809 defined by a body of the medical device 100, a side-port 600 in fluid communication with the lumen, and a closed distal end. Distal portion 830 has an outer diameter less than the outer diameter of distal portion 112 proximal of the change in diameter 831, i.e., distal portion 830 has a reduced diameter. In the embodiment of FIG. 4A, distal tip 403 of the medical device comprises a distal electrode 106. Some alternative embodiments of medical device 100 do not include an electrode. Tubular member 800 defines tubular member lumen 802. Tubular member 800 and distal portion 830 of medical device 100, in combination, define conduit 808 whereby medical device 100 is able to provide sufficient fluid flow for delivering contrast fluid to stain tissue. Fluid (e.g. blood) may also be withdrawn through the path defined by conduit 808, side-port 600, and device lumen 809. In the example of FIG. 4A, conduit 808 includes the space between tubular member 800 and reduced diameter distal portion 830, and the portion of tubular member lumen 802 distal of medical device 100.

In the embodiment of FIG. 4A, distal portion 830 is distal of change in diameter 831 and includes insulated part 834 and electrode 106. Constant diameter part 836 is distal of change in diameter 831 and includes insulated part 834 and the straight longitudinal part of electrode 106 that has a constant diameter (i.e. the portion of electrode proximal of the dome shaped electrode tip). Constant diameter part 836 of distal portion 830 does not taper and may be described as having a substantially constant diameter longitudinally. There is a minor change in outer diameter at the distal end of electrical insulation 104, but with regards to fluid flow, it can be considered negligible.

In the embodiment of FIG. 4A, a small space or gap 832 exists between the tubular member 800 and the part of distal portion 112 proximal of the change in diameter 831. It is common for embodiments of medical device 100 and tubular member 800 to have a small gap 832 between the outer diameter of medical device and the inner diameter of tubular member. Completely eliminating the gap would result in increased friction between the medical device and tubular member and could result in difficulty advancing medical device 100 through tubular member 800. In typical embodiments, the gap is small enough that it prevents a substantial flow of fluids such as contrast fluids, which are typically 3 to 5 times more viscous than water.

In the embodiment of FIG. 4A, side-port 600 is close to the change in diameter 831 whereby the larger diameter part of distal portion 112 functions as a brace to keep tubular member 800 from blocking side-port 600. FIG. 4A illustrates an abrupt change in diameter. Alternative embodiments have a less abrupt change in diameter. Typical embodiments of medical device 100 include a second side-port, with the two side-ports being opposite to each other. Some alternative embodiments include more than two side-ports. Other alternative embodiments have one side-port. In some alternative embodiments of medical device 100, side-port 600 is longitudinally elongated, i.e., capsule-shaped.

The side-port(s) 600 and the device lumen 809 together provide a pressure transmitting lumen. The pressure transmitting lumen is operable to be coupled to a pressure transducer, for example, external pressure transducer 708 (to be described with respect to FIG. 8).

Distal tip 403 of medical device 100 is shown in the example of FIG. 4A as being slightly proximal of the distal end of tubular member 800. In this position, fluid communication between the medical device lumen and the surrounding environment may be established. Fluid communication may also be established when distal tip 403 is positioned further proximal of the distal end of tubular member 800, when distal tip 403 is aligned with the distal end of tubular member 800, and when distal tip 403 is positioned distal of the distal end of tubular member 800. If distal tip 403 is positioned such that side-port 600 is distal of the distal end of tubular member 800, it is still possible to deliver fluid in a radial direction.

Typical embodiments of medical device 100 comprise a conductive member (elongate member 102, or main member 210 joined to end member 212), which is typically comprised of a metallic material. The conductive member is in electrical communication with distal electrode 106, and a layer of insulation (electrical insulation 104) covers the metallic material. In other words, the elongate member 102 comprises an electrically conductive material, and a layer of insulation covers the electrically conductive material, the electrically conductive material being electrically coupled to the electrode 106. For some single piece embodiments, elongate member 102 has an on outer diameter proximal of change in diameter 831 of about 0.7 mm to about 0.8 mm at distal end 206, and an outer diameter for reduced diameter distal portion 830 of about 0.4 mm to about 0.62 mm. For some two piece embodiments, end member 212 has an outer diameter proximal of change in diameter 831 of about 0.40 mm to about 0.80 mm, and an outer diameter for distal portion 830 of about 0.22 mm to about 0.62 mm. The above described embodiments are typically used with a tubular member defining a corresponding lumen about 0.01 mm (0.0005 inches) to about 0.04 mm (0.0015 inches) larger than the outer diameter of medical device 100 proximal of change in diameter 831.

FIG. 4B illustrates an end view of the apparatus of FIG. 4A. The figure includes, from inside to outside (in solid line), electrode 106, electrical insulation 104, the part of distal portion 112 proximal of change in diameter 831, gap 832, tubular member distal end 801, and tubular member 800. Hidden features shown in broken line include side-port 600 and device lumen 809.

In the embodiment of FIGS. 4A and 4B, distal tip 403 of the medical device is comprised of electrode 106 which defines a substantially circular cross-section and a circular end-profile. Similar to the embodiments of FIGS. 3A and 3B, electrode 106 of FIG. 4B is at the end of elongate member 102 (or end member 212) and has the same outer diameter as the distal end of the conductive member. Since constant diameter part 836 of reduced diameter distal portion 830 does not substantially taper (the small change in diameter at the distal end of electrical insulation 104 is not taken to be substantial), electrode 106 has a diameter which is substantially equal to the diameter of the part of distal portion 830 which is proximal of electrode 106 (i.e. substantially equal to the diameter of insulated part 834).

Making reference again to FIGS. 1 to 4, some embodiments of medical device 100 comprise an elongate member 102 having a closed distal end, with the elongate member defining a device lumen 809 and at least one side-port 600 in fluid communication with the device lumen. The elongate member also defines a proximal portion and a distal portion 830, the distal portion extending from the at least one side-port 600 to the distal end of the elongate member. The proximal portion defines a first outer diameter and the distal portion defines a second outer diameter, with the first outer diameter being larger than the second outer diameter, and the second outer diameter being substantially constant. The distal tip of medical device 100 comprises an electrode 106. The diameter of the electrode is substantially equal to the second outer diameter.

Some embodiments of electrode 106 typically create a puncture in tissue with a diameter 10 to 20 percent larger than the electrode. Such a puncture diameter is typically large enough to facilitate passage of the part of medical device proximal of change of diameter 831 (i.e. the larger diameter portion of medical device) through the tissue puncture, and to start advancing a dilator over medical device 100 and through the tissue.

Figure 5B:
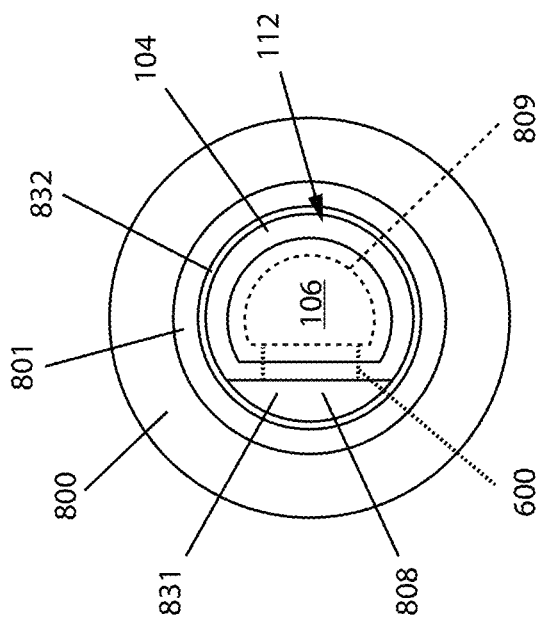
FIGS. 5A and 5B illustrate a partially cut-away side view and an end view, respectively, of a medical device and a tubular member in accordance with another embodiment of the present invention.
Figure 5A:
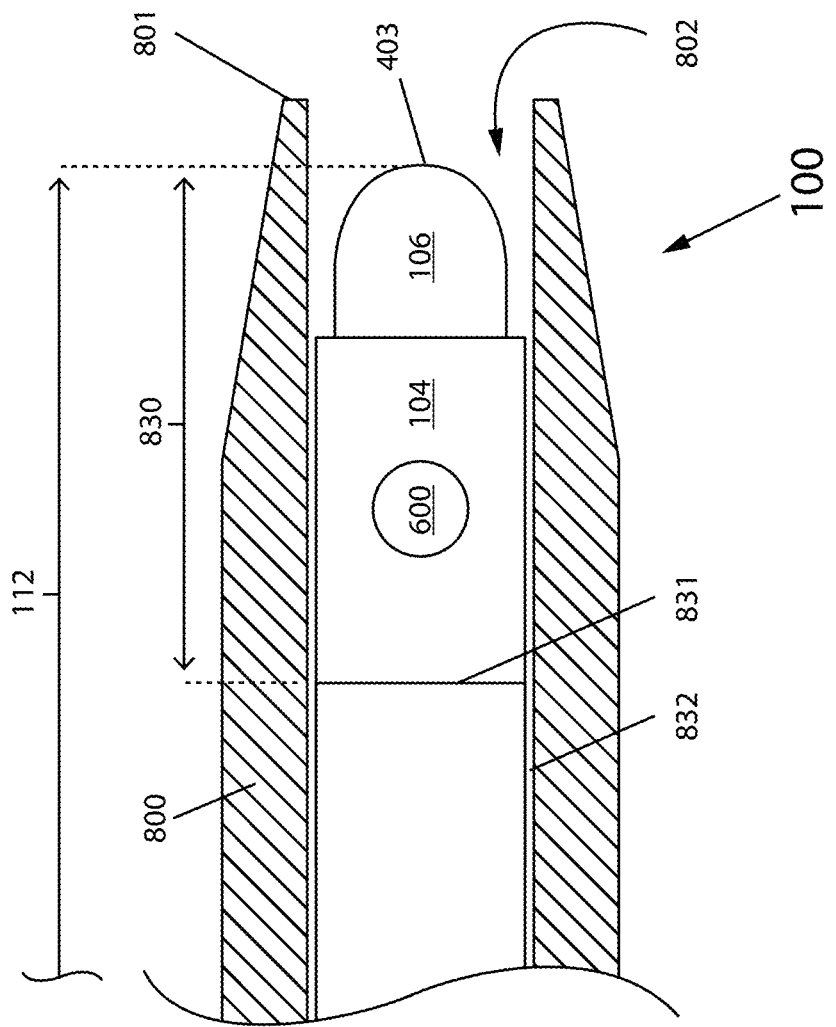

FIGS. 5A to 5D illustrate embodiments of medical device 100 wherein distal portion 830 has a non-circular cross section. In FIGS. 5A and 5B, distal portion 830 (including electrode 106 and insulated part 834 (FIG. 4*a*)) defines a substantially flat outer surface portion. The body of medical device 100 defines device lumen 809 (shown in broken line in FIG. 5B), and side-port 600 in fluid communication with the lumen. Reduced outer diameter distal portion 830 of the body extends between side-port 600 and distal tip 403 of the medical device whereby the outer surface of medical device 100, in combination with tubular member 800 can provide a conduit 808. While FIG. 5A illustrates a portion of reduced outer diameter distal portion 830 extending proximally from side-port 600 to change in diameter 831, some alternative embodiments do not include this portion, i.e., change in diameter 831 is adjacent side-port 600.

The embodiment of conduit 808 in FIG. 5B is shown as having an end-view shape of a portion of circle. The reduced outer diameter is substantially constant longitudinally along distal portion 830, with the exceptions of the distal end of electrical insulation 104 and the hemispherical-shaped distal tip of electrode 106. A cross-section of the electrode 106 is substantially identical to a cross-section of the part of the distal portion 830 which is proximal of the electrode.

Figure 5D:
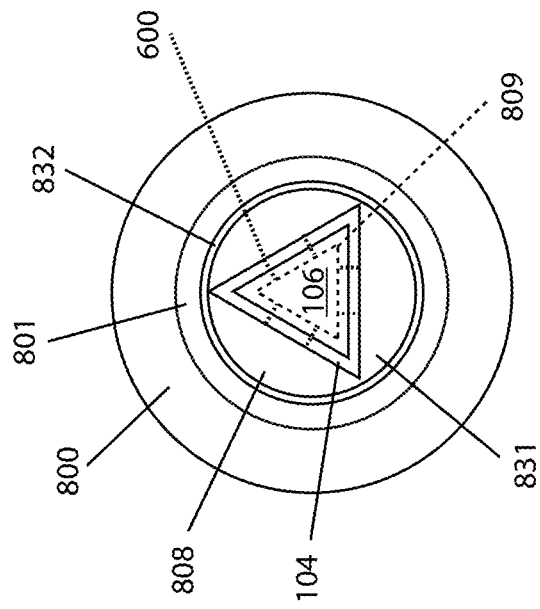
FIGS. 5C and 5D illustrate end views of a medical device and a tubular member in accordance with alternative embodiments of the present invention.
Figure 5C:
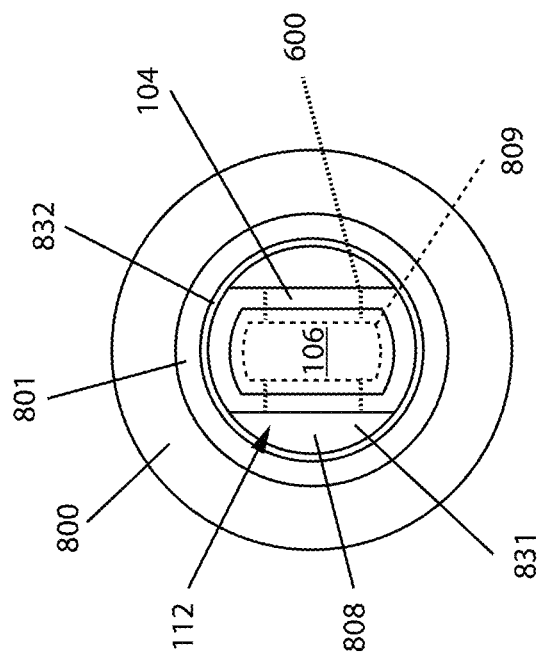

FIG. 5C illustrates an alternative embodiment with two flat outer surfaces and two corresponding side-ports. FIG. 5D illustrates another alternative embodiment with three flat outer surfaces and three corresponding side-ports. Further alternative embodiments are similar to the embodiments of FIGS. 5B, 5C and 5D, except instead of the flat outer surfaces, the devices have corresponding outer surfaces that are convexly curved to provide a larger device lumen 809.

Figure 6B:
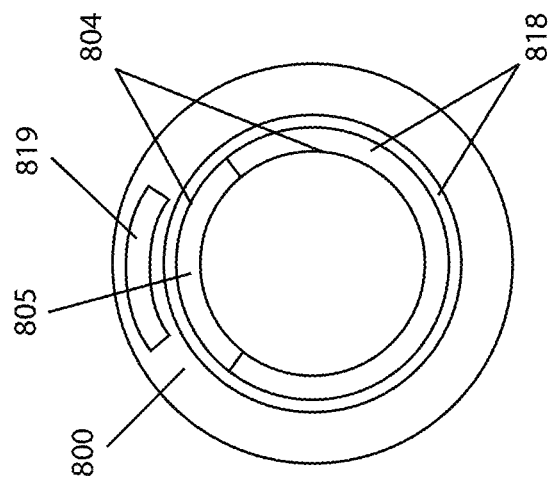
FIGS. 6A and 6B illustrate a partially cut-away side view and an end view, respectively, of a tubular member in accordance with another embodiment of the present invention.
Figure 6A:
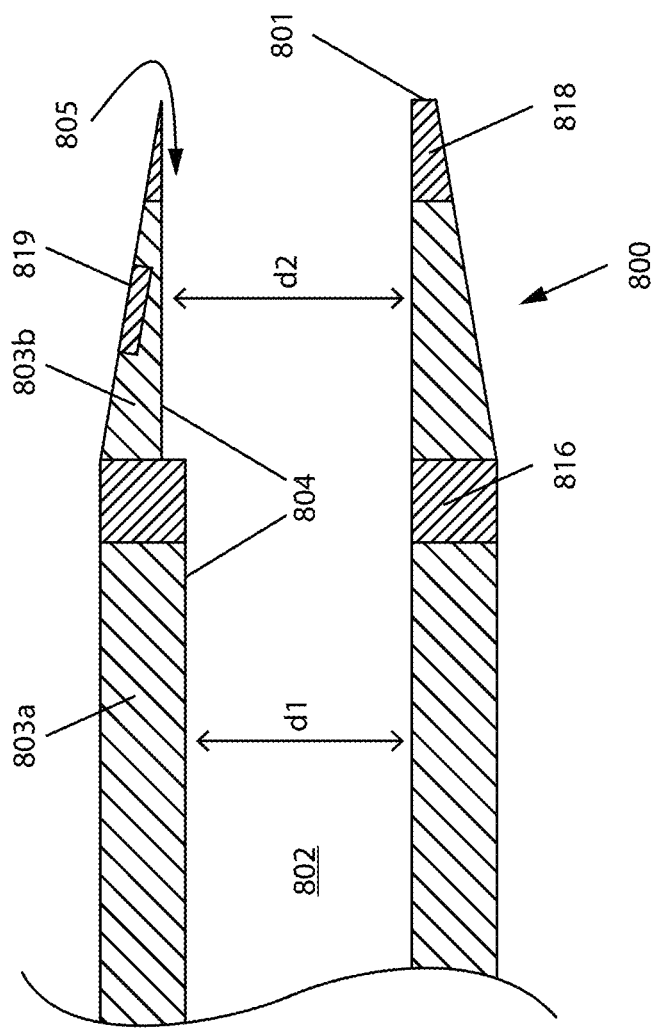

FIGS. 6A and 6B illustrate an embodiment of a tubular member 800 for use with a medical device 100 having a side-port 600. The body of tubular member 800 defines a lumen such that tubular member proximal region 803*a* has a first inner diameter d1, and tubular member distal region 803*b* has at least a portion of it defining a second inner diameter d2, wherein the second inner diameter d2 is greater than the first inner diameter d1, and wherein the tubular member distal region 803*b* extends to the tubular member distal end 801.

The embodiment of FIG. 6B includes the tubular member distal region 803*b* (i.e. the increased diameter portion with the second inner diameter d2) extending circumferentially over less than 360 degrees of the circumference of the tubular member. Tubular member inner surface 804 defines a tubular member channel 805 which, in the example of FIG. 6B, extends circumferentially approximately 90 degrees. In some alternative embodiments, tubular member distal region 803*b* extends 360 degrees of the circumference of the tubular body.

The embodiment of FIGS. 6A and 6B includes tubular member proximal marker 816 at the proximal end of the distal region, and tubular member distal marker 818 at the distal end of tubular member distal region 803*b*. Alternative embodiments have only one of the distal region markers or neither distal region marker. The embodiment of FIGS. 6A and 6B also includes a side marker 819, which is operable to be used as an orientation marker for aligning the tubular member distal region 803*b* (i.e. the increased diameter portion) with the side-port 600 of a medical device 100 positioned inside the tubular member.

One embodiment is a dilator comprising a tubular member defining a lumen in fluid communication with a distal end aperture, a proximal region having a first inner diameter, and a distal region having an increased diameter portion. The increased diameter portion extends proximally from a distal end of the dilator and defines a substantially longitudinally constant second inner diameter that is greater than the first inner diameter.

Figure 7B:
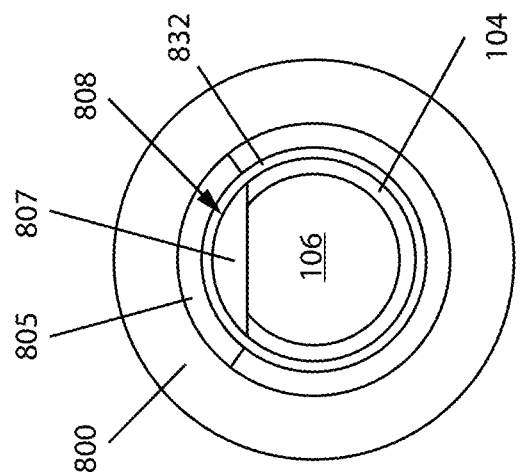
FIGS. 7A and 7B illustrate a partially cut-away side view and an end view, respectively, of a medical device and a tubular member in accordance with another embodiment of the present invention.
Figure 7A:
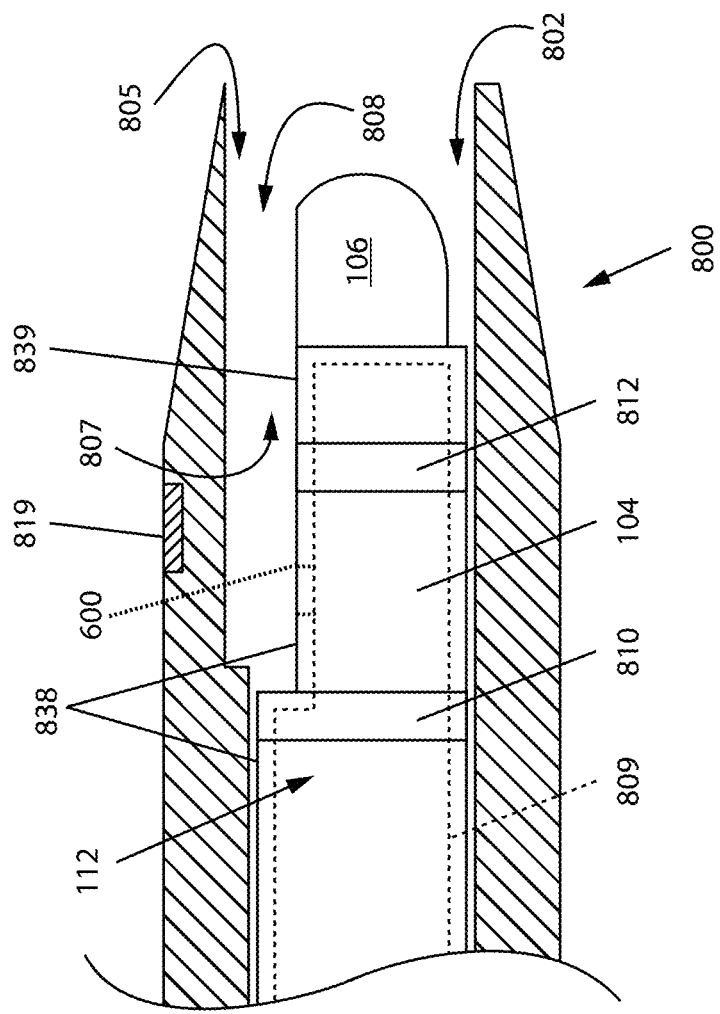

The embodiment of FIGS. 7A and 7B is a kit comprising a tubular member 800 and a medical device 100, operable to be combined to form an apparatus. Tubular member 800 defines a tubular member lumen 802 for receiving medical device 100. Medical device 100 defines a device lumen 809 in fluid communication with a side-port 600, and comprises a medical device proximal region 838 proximal of the side-port, and a medical device distal region 839 distal of the side-port. Medical device 100 and tubular member 800 are configured for cooperatively forming a conduit 808 between an outer surface of medical device distal region 839 and an inner surface of tubular member 800. In the example of FIG. 7A, conduit 808 is formed both proximal and distal of side-port 600, while in alternative embodiments it is only formed distal of the side-port. In typical use, conduit 808 is formed at least between the side-port and a distal end of the tubular member when medical device 100 is inserted and positioned within tubular member lumen 802.

The apparatus of FIG. 7A includes both a tubular member channel 805 and a medical device channel 807. Conduit 808 is comprised of both tubular member channel 805 and a medical device channel 807. In typical embodiments, at least some of the length of conduit 808 has a constant cross-sectional configuration, which reduces turbulence and facilitates laminar flow, which in turn facilitates forwards injection of a fluid. Some alternative embodiments include a tubular member channel 805 but not a medical device channel 807, and some other alternative embodiments include a medical device channel 807 but not a tubular member channel 805.

Some embodiments of the medical device and the tubular member further comprise corresponding markers for aligning the side-port of the medical device within the tubular member lumen to form said conduit. In the example of FIG. 7, medical device 100 includes medical device proximal marker 810 and medical device distal marker 812, while tubular member 800 includes side marker 819. In some embodiments of the kit, the corresponding markers are configured for longitudinally aligning the side-port within the tubular member lumen. In the example of FIG. 7, side-port 600, which is equidistant between medical device proximal marker 810 and medical device distal marker 812, can be longitudinally aligned with side marker 819 by positioning side marker 819 between medical device proximal marker 810 and medical device distal marker 812.

In some embodiments of the kit, the corresponding markers are configured for rotationally aligning the side-port within the tubular member lumen. In the example of FIG. 7, side-port 600 can be rotationally aligned with side marker 819 of tubular member 800 by comparing the relatively larger diameter medical device proximal marker 810 with the smaller diameter medical device distal marker 812, which thereby aligns side-port 600 with tubular member channel 805. Alternative embodiments of medical device 100 include a side-marker on the same side as side-port 600, or on the side opposite to the side-port, to facilitate rotational positioning. Further details regarding markers are found in U.S. Pat. No. 4,774,949, issued Oct. 4, 1988 to Fogarty, incorporated by reference herein in its entirety.

An embodiment of a kit comprises a tubular member defining a tubular member lumen in fluid communication with a distal end aperture, and a medical device having a closed distal end. The medical device comprises a device lumen in fluid communication with at least one side-port, and a distal portion extending from the at least one side-port to a distal end of the medical device. Medical device and tubular member are configured to cooperatively form a conduit between an outer surface of the distal portion and an inner surface of the tubular member when the medical device is inserted within the tubular member lumen. The conduit extends at least between the side-port and the distal end aperture for enabling fluid communication between the side-port and an environment external to the distal end aperture.

In a specific embodiment of a kit, end member 212 has an on outer diameter proximal of change in diameter 831 of about 0.032 inches (about 0.81 mm), and an outer diameter at reduced diameter distal portion 830 of about 0.020 inches (about 0.51 mm) to about 0.025 inches (about 0.64 mm). End member 212 is used with a tubular member defining a lumen about 0.0325 inches (0.82 mm) to about 0.0335 inches (0.85 mm).

Figure 8:
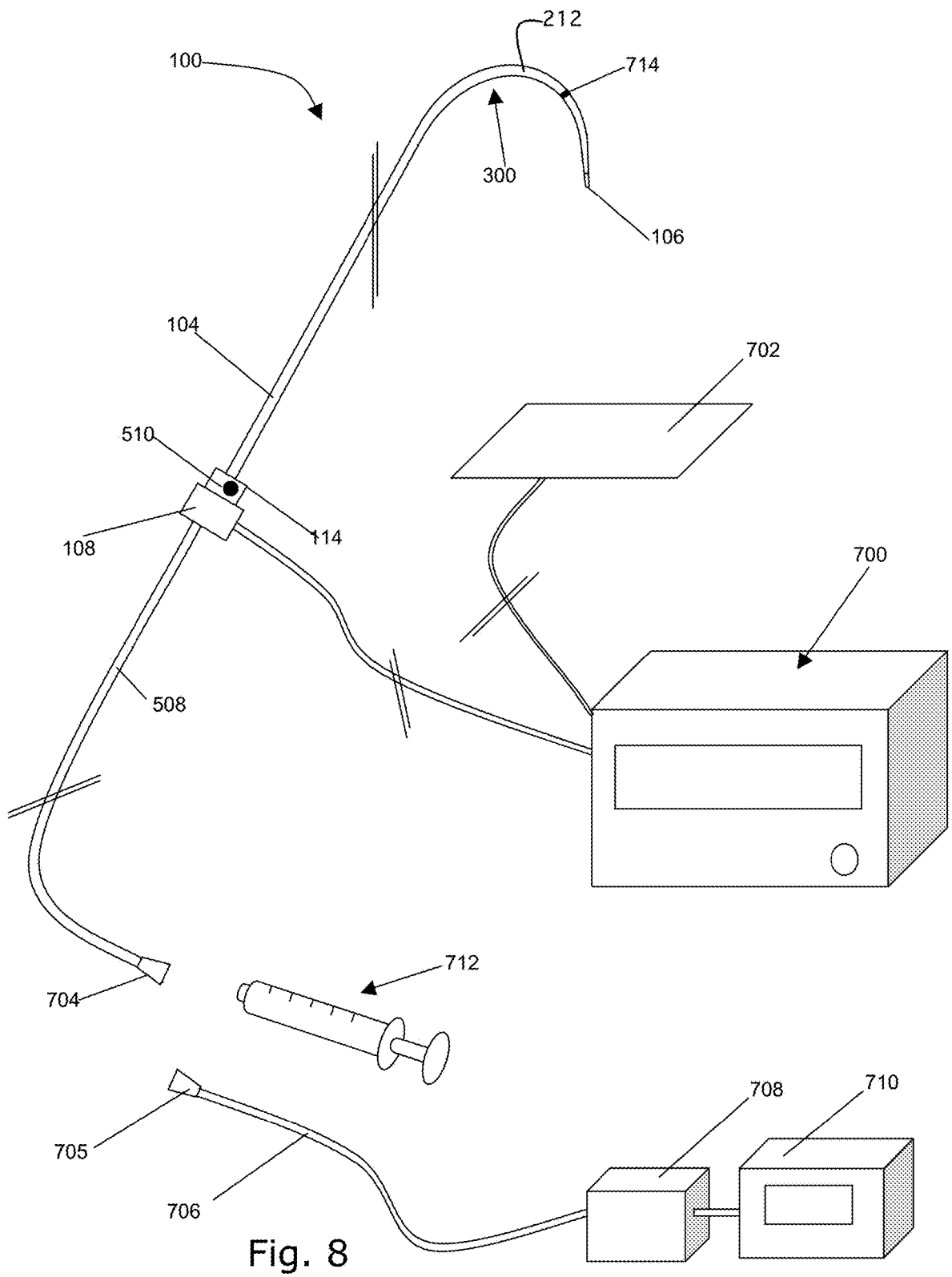
FIG. 8 illustrates a perspective view of a system including a medical device in accordance with the present invention.

Referring to FIG. 8, systems for use with the medical device 100 typically comprise a generator 700 and, in some embodiments, a grounding pad 702, external tubing 706, a pressure transducer 708, and/or a source of fluid 712.

Referring to FIG. 8, as mentioned herein above, in order to measure pressure at the distal region 202 (FIG. 10) of the medical device 100, an external pressure transducer may be coupled to the medical device 100. In the example of FIG. 8, an adapter 705 is operatively coupled to the external tubing 706, which is operatively coupled to an external pressure transducer 708. The adapter 705 is structured to couple to adapter 704 when in use. In some examples, adapters 704 and 705 comprise male and female Luer locks or other fluid connectors, adapted to readily couple and decouple to/from each other. In use, tubing 706 and 508 may be flushed with saline or another suitable fluid to remove air bubbles prior to measuring pressure. When medical device 100 is positioned in a vessel, conduit, or cavity of a body, fluid adjacent the distal region 202 (FIG. 10) exerts pressure through the side-port(s) 600 on fluid within the lumen 208, which in turn exerts pressure on fluid in tubing 508 and 706, which further exerts pressure on external pressure transducer 708. The side-port(s) 600 and the lumen 208 thus provide a pressure sensor in the form of a pressure transmitting lumen for coupling to a pressure transducer.

The external pressure transducer 708 produces a signal that varies as a function of the pressure it senses. The external pressure transducer 708 is electrically coupled to a pressure monitoring system 710 that is operative to convert the signal provided by the transducer 708 and display, for example, a pressure contour as a function of time. Thus, pressure is optionally measured and/or recorded and, in accordance with one embodiment of a method aspect as described further herein below, used to determine a position of the distal region 202. In those embodiments of the medical device 100 that do not comprise a lumen in fluid communication with the outside environment, a pressure transducer may be mounted at or proximate to the distal portion 112 of the medical device 100 and coupled to a pressure monitoring system, for example, via an electrical connection.

As previously mentioned, for some embodiments the medical device 100 is operatively coupled to a source of fluid 712 for delivering various fluids to the medical device 100 and thereby to a surrounding environment. The source of fluid 712 may be, for example, an IV bag or a syringe. The source of fluid 712 may be operatively coupled to the lumen 208 via the tubing 508 and the adapter 704, as mentioned herein above. Alternatively, or in addition, some embodiments include the medical device 100 being operatively coupled to an aspiration device for removing material from the patient's body through one or more of the side-ports 600.

In one broad aspect, the medical apparatus is used in a method of establishing a conduit for fluid communication for a medical device 100, the medical device defining a device lumen 809 in fluid communication with a side-port 600. Making reference to FIGS. 4 to 9, the method comprises the steps of (a) inserting a medical device 100 having at least one side-port 600 into a tubular member 800, and (b) cooperatively defining a conduit 808 for fluid communication by positioning the side-port 600 of the medical device 100 at a location of the tubular member 800 where a space exists between the side-port 600 and a tubular member inner surface 804, the space extending at least between the side-port 600 and a distal end of the tubular member.

In some embodiments of the broad aspect, the medical device comprises a medical device proximal marker 810 proximal of the side-port, and a medical device distal marker 812 distal of the side-port, and step (b) includes visualizing at least one of the proximal marker and the distal marker to position the medical device. In some such embodiments, step (b) comprises positioning side-port 600 within tubular member lumen 802, for example, by using a medical device proximal marker 810 and a medical device distal marker 812. In such embodiments of the method, it is not necessary for distal tip 403 to be inside of tubular member lumen 802. In some embodiments of the method, the medical device further comprises a side-port marker wherein the side-port marker and the side-port are equidistant from a tip of the medical device, and wherein step (b) includes visualizing the side-port marker to position the medical device. In some other embodiments, step (b) comprises positioning distal portion 830 of distal portion 112 within tubular member lumen 802, which inherently positions the side-port in the tubular member lumen. In some embodiments of the method, step (b) includes aligning a distal tip 403 of the medical device with the tubular member distal end 801.

Some embodiments of the broad aspect further comprise a step (c) of delivering fluid through the side-port 600, wherein the fluid is a contrast fluid 814 and wherein step (c) includes delivering the contrast fluid distally through the distal end of the tubular member. Some such embodiments further comprise a step of delivering electrical energy to puncture tissue before the contrast fluid is delivered. Some embodiments comprise a step (d) of delivering electrical energy through the medical device to create a puncture through a tissue after the contrast fluid is delivered.

In some embodiments, the tissue comprises a septum of a heart, and step (c) comprises staining the septum by delivering contrast fluid through the side-port.

In some embodiments of the broad aspect, the side-port 600 and the device lumen 809 together comprise a pressure transmitting lumen, and the method further comprises a step (c) of measuring a pressure of an environment external to the distal end using the side-port and the conduit. Some such embodiments further comprise a step (d) of delivering fluid through the side-port.

Some embodiments of the broad aspect further comprise a step (c) of withdrawing fluid through the side-port 600. In some such embodiments, the fluid is blood.

Figure 9A:
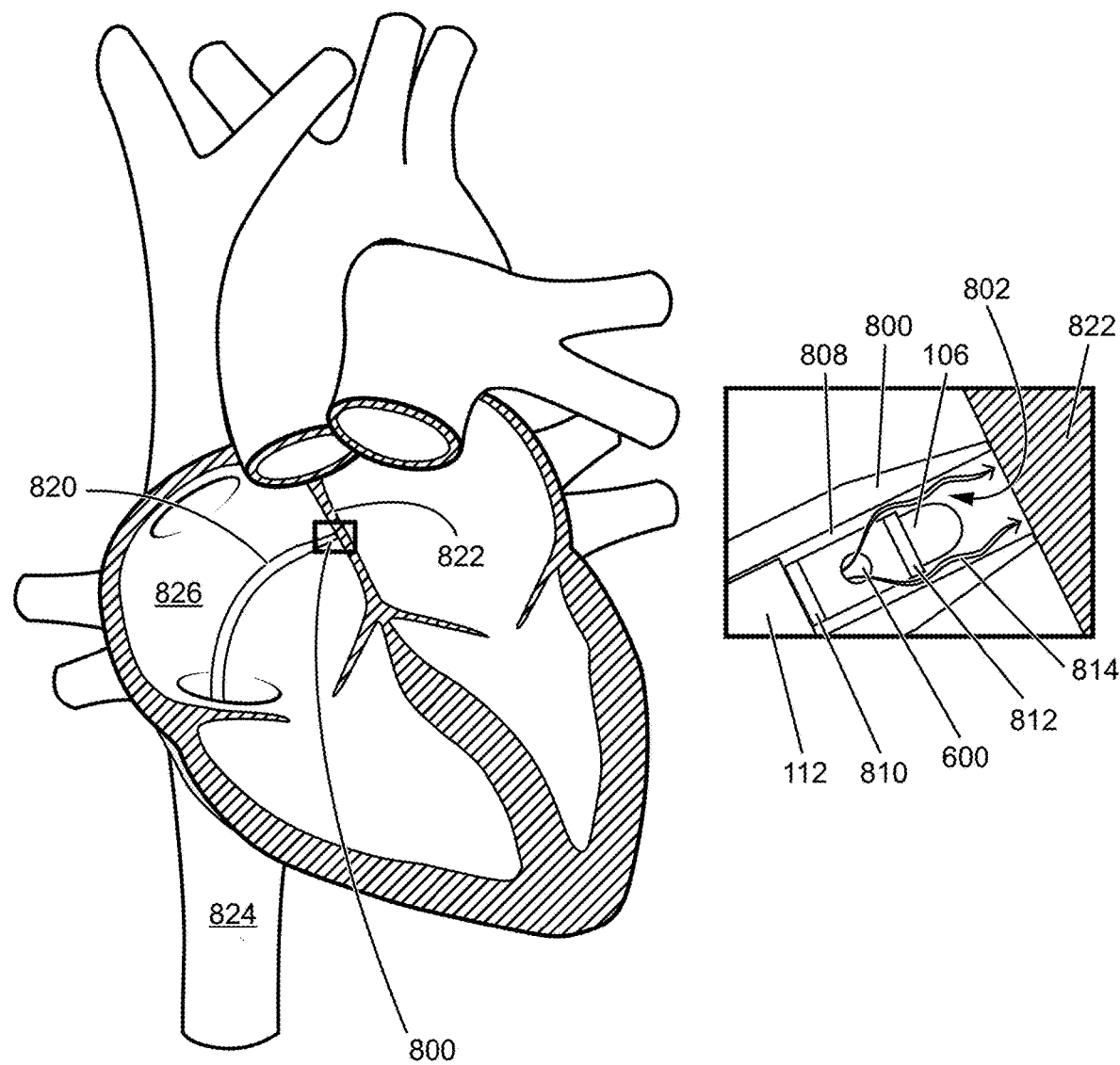
FIGS. 9A and 9B illustrate partially cut-away views of a method using an apparatus in accordance with an embodiment of the present invention.
Figure 9B:
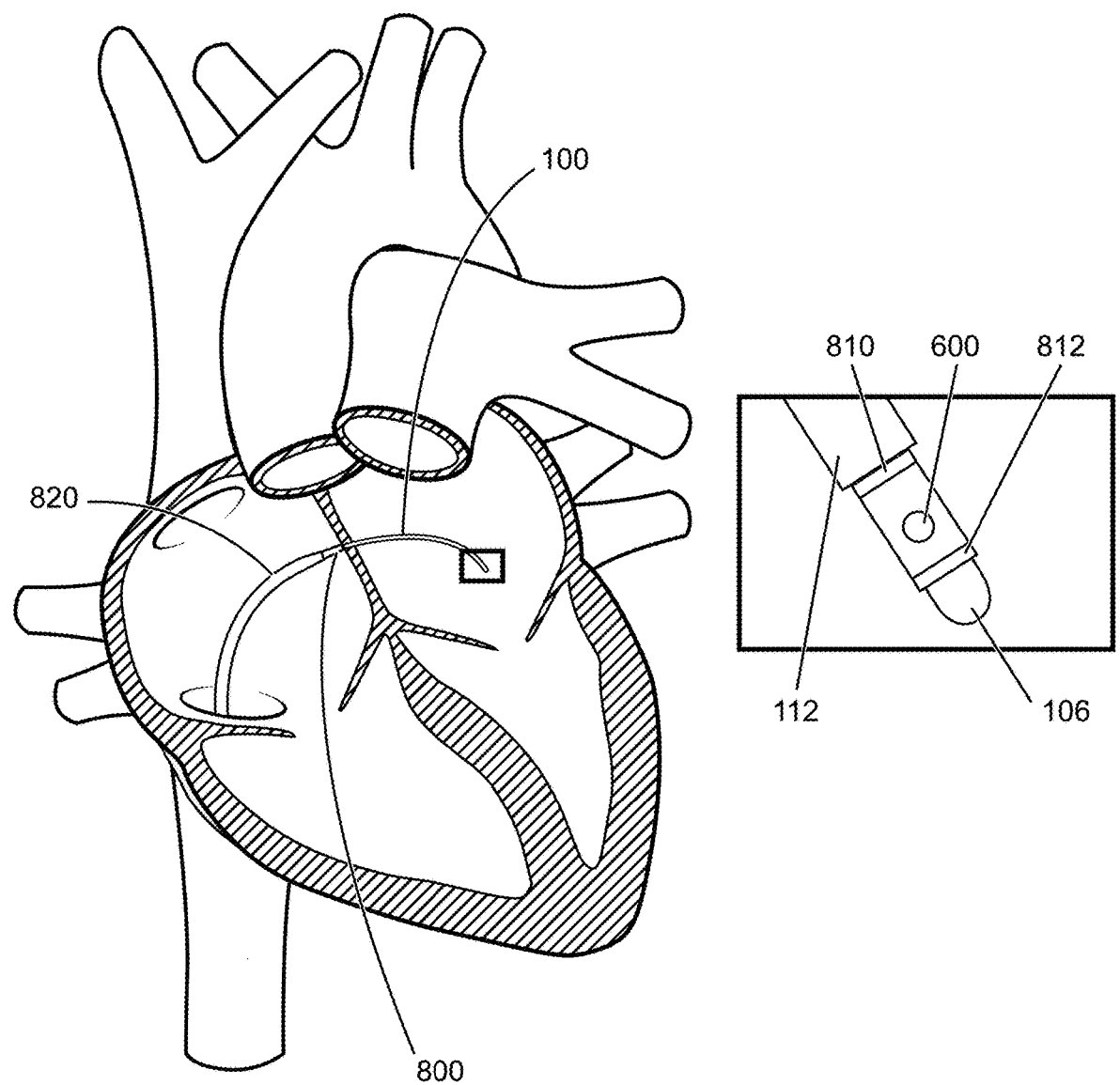
Figure 10A:
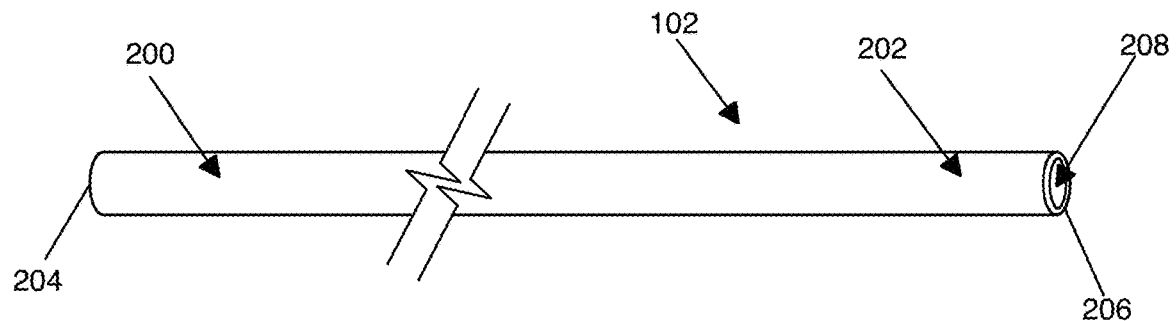
FIG. 10A illustrates a perspective view of an elongate member portion of the medical device shown in FIG. 1.
Figures 10B, 10C, 10D:
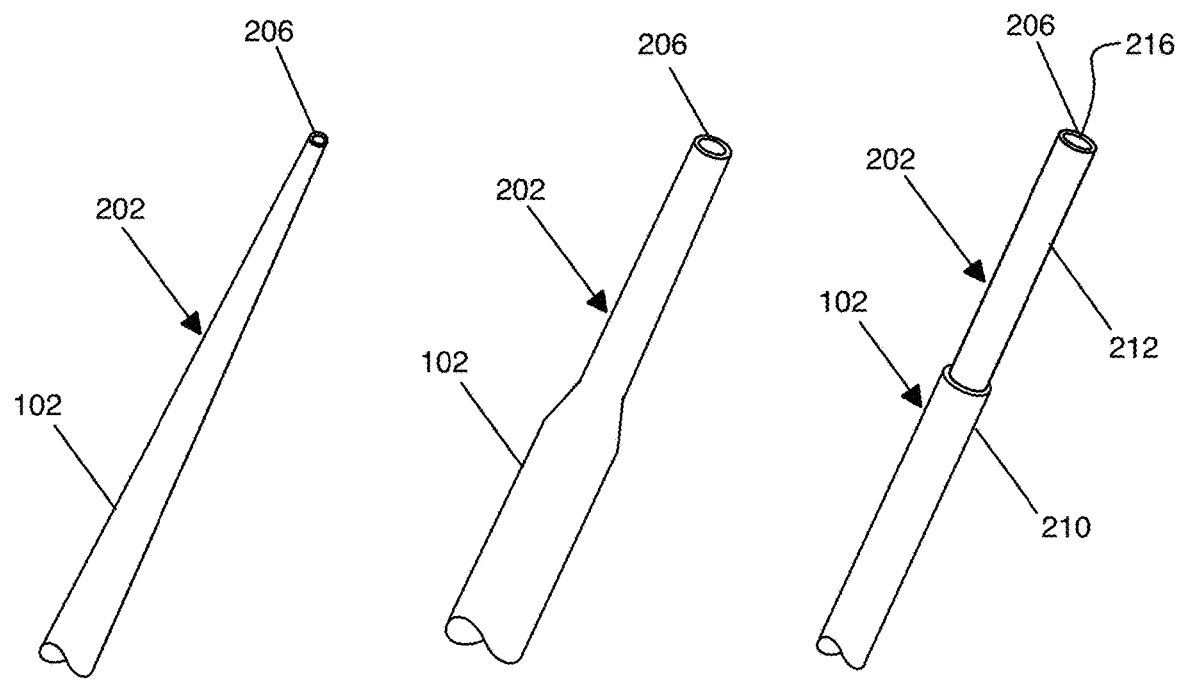
FIG. 10B illustrates a partial perspective view of an alternative elongate member usable in the medical device shown in FIG. 1.
FIG. 10C illustrates a partial perspective view of another alternative elongate member usable in the medical device shown in FIG. 1.
FIG. 10D illustrates a partial perspective view of yet another alternative elongate member usable in the medical device shown in FIG. 1.

In one example of a method of use, illustrated in FIGS. 9A and 9B, a target site comprises the atrial septum 822, a tissue within the heart of a patient. In this example, the target site is accessed via the inferior vena cava (IVC), for example, through the femoral vein. The medical device 100 of FIGS. 9A and 9B is similar to medical device of FIG. 4A, except the embodiment of FIG. 9 has a medical device proximal marker 810 and a medical device distal marker 812.

The example of the method includes a user advancing sheath 820 and a dilator (i.e. tubular member 800) through inferior vena cava 824, and introducing the sheath and tubular member 800 into the right atrium 826 of the heart. An electrosurgical device, for example medical device 100 described herein above, is then introduced into tubular member lumen 802, and advanced toward the heart. In typical embodiments of the method, these steps are performed with the aid of fluoroscopic imaging.

After inserting medical device 100 into tubular member 800, the user positions the distal end of tubular member 800 against the atrial septum 822 (FIG. 9A). Some embodiments of tubular member 800 include markers (FIG. 6A). The medical device is then positioned such that electrode 106 is aligned with or slightly proximal of the distal end of tubular member 800 (FIG. 9A insert). Medical device proximal marker 810 and medical device distal marker 812 facilitate positioning medical device 100. Tubular member 800 is typically positioned against the fossa ovalis of the atrial septum 822. Referring to the FIG. 9A insert, the inner surface of tubular member 800 and the outer surface of medical device 100 define conduit 808 from side-port 600 to the distal end of tubular member lumen 802, which is sealed by atrial septum 822.

Once medical device 100 and tubular member 800 have been positioned, additional steps can be performed, including taking a pressure measurement and/or delivering material to the target site, for example, a contrast agent, through side-port(s) 600. The FIG. 9A insert illustrates contrast fluid 814 flowing from side-port 600, through conduit 808, and ending at atrial septum 822, whereby the tissue is stained by the contrast fluid. In alternative examples, electrode 106 is positioned against atrial septum 822 when contrast fluid 814 is delivered. Such steps facilitate the localization of the electrode 106 at the desired target site.

Starting from the position illustrated by the FIG. 9A insert, medical device 100 is advanced until electrode 106 contacts atrial septum 822. (Alternative embodiments wherein electrode 106 is positioned against atrial septum 822 when contrast fluid 814 is delivered do not require this repositioning.) With the medical device 100 and the dilator (i.e. tubular member 800) positioned at the target site, energy is delivered from an energy source, through medical device 100, to the target site. The path of energy delivery is through elongate member 102 (or main member 210 and end member 212), to the electrode 106, and into the tissue at the target site. The example of FIG. 9A includes delivering energy to vaporize cells in the vicinity of the electrode, thereby creating a void or puncture through the tissue at the target site, and advancing distal portion 112 of the medical device 100 at least partially through the puncture. When the distal portion 112 has passed through the target tissue and reached the left atrium (FIG. 9B), energy delivery is stopped. The side-ports of medical device 100 are uncovered (FIG. 9B insert), whereby contrast may be delivered to confirm the position of distal portion 112 in the left atrium of the heart. The diameter of the puncture created by the delivery of energy is typically large enough to facilitate advancing distal portion 112 of the medical device 100 therethrough and to start advancing a dilator (i.e. tubular member 800).

Referring now to FIG. 10A, the elongate member 102 includes a proximal region 200, a distal region 202, a proximal end 204, and a distal end 206. In some embodiments of the invention, the elongate member 102 defines a lumen 208, which typically extends substantially between the proximal region 200 and the distal region 202.

The elongate member 102 is typically sized such that the handle 110 remains outside of the patient when the distal end 206 is within the body, for example, adjacent the target site. That is, the proximal end 204 is at a location outside of the body, while the distal end 206 is located within the heart of the patient. Thus, in some embodiments of the invention, the length of the elongate member 102, i.e., the sum of the force transmitting length and the distal portion length, is between about 30 cm and about 100 cm, depending, for example, on the specific application and/or target site.

The transverse cross-sectional shape of the elongate member 102 may take any suitable configuration, and the invention is not limited in this regard. For example, the transverse cross-sectional shape of the elongate member 102 is substantially circular, ovoid, oblong, or polygonal, among other possibilities. Furthermore, in some embodiments, the cross-sectional shape varies along the length of the elongate member 102. For example, in one embodiment, the cross-sectional shape of the proximal region 200 is substantially circular, while the cross-sectional shape of the distal region 202 is substantially ovoid.

In typical embodiments, the outer diameter of the elongate member 102 is sized such that it fits within vessels of the patient's body. For example, in some embodiments, the outer diameter of the elongate member 102 is between about 0.40 mm and about 1.5 mm (i.e. between about 27 Gauge and about 17 Gauge). In some embodiments, the outer diameter of the elongate member 102 varies along the length of the elongate member 102. For example, in some embodiments, the outer diameter of the elongate member 102 tapers from the proximal end 204 towards the distal end 206. In one specific embodiment, the outer diameter of the proximal region 200 of the elongate member 102 is about 1.5 mm. In this embodiment, at a point about 4 cm from the distal end 206, the outer diameter begins to decrease such that the distal end 206 of the elongate member 102 is about 0.7 mm in outer diameter. In a further embodiment, the outer diameter of the elongate member 102 tapers from about 1.3 mm to about 0.8 mm at a distance of about 1.5 mm from the distal end 206. FIG. 10B is an example of a taper in elongate member 102 occurring smoothly, for example, over a length of about 4 cm. FIG. 10C is an example of a taper occurring more abruptly, for example, over a length of about 1 mm or less. The taper may be applied to the elongate member 102 by a variety of methods. In some embodiments, the elongate member 102 is manufactured with the taper already incorporated therein. In other embodiments, the elongate member 102 is manufactured without a taper, and the taper is created by swaging the elongate member down to the required outside diameter, or by machining the distal region 202 such that the outside diameter tapers while the inside diameter remains constant.

In a further embodiment, the elongate member 102 is manufactured from two pieces of material, each having a different diameter, which are joined together. For example, as shown in FIG. 10D, the elongate member 102 includes a main member 210 mechanically coupled to the handle (not shown in FIG. 10D), the main member 210 having a length of about 50 cm to about 100 cm and an outer diameter of about 1.15 mm to about 1.35 mm. The main member 210 defines a main member lumen 214, as shown in FIG. 2E, extending substantially longitudinally therethrough. The main member is co-axially joined to an end member 212, having a length of about 2.5 cm to about 10 cm and an outer diameter of about 0.40 mm to about 0.80 mm. In some examples, the end member 212 is inserted partially into the main member lumen 214, substantially longitudinally opposed to the handle 110. In some embodiments, the electrode 106 is located about the end member, for example, by being mechanically coupled to the end member 212, while in other embodiments the electrode 106 is integral with the end member 212. If the end member 212 defines an end member lumen 216, as seen in FIGS. 10D and 2E, the end member lumen 216 is in fluid communication with the main member lumen 214, as shown in FIG. 2E. The main member 210 and the end member 212 are joined in any suitable manner, for example welding, soldering, friction fitting, or the use of adhesives, among other possibilities. Also, in some embodiments, the main member lumen 214 and the end member lumen 216 have substantially similar diameters, which reduces turbulence in fluids flowing through the main member lumen 214 and the end member lumen 216.

In embodiments of the invention wherein the elongate member 102 defines a lumen 208, the wall thickness of the elongate member 102 may vary depending on the application, and the invention is not limited in this regard. For example, if a stiffer device is desirable, the wall thickness is typically greater than if more flexibility is desired. In some embodiments, the wall thickness in the force transmitting region is from about 0.05 mm to about 0.40 mm, and remains constant along the length of the elongate member 102. In other embodiments, wherein the elongate member 102 is tapered, the wall thickness of the elongate member 102 varies along the elongate member 102. For example, in some embodiments, the wall thickness in the proximal region 200 is from about 0.1 mm to about 0.4 mm, tapering to a thickness of from about 0.05 mm to about 0.20 mm in the distal region 202. In some embodiments, the wall tapers from inside to outside, thereby maintaining a consistent outer diameter and having a changing inner diameter. Alternative embodiments include the wall tapering from outside to inside, thereby maintaining a consistent inner diameter and having a changing outer diameter. Further alternative embodiments include the wall of the elongate member 102 tapering from both the inside and the outside, for example, by having both diameters decrease such that the wall thickness remains constant. For example, in some embodiments the lumen 208 has a diameter of from about 0.4 mm to about 0.8 mm at the proximal region 200, and tapers to a diameter of from about 0.3 mm to about 0.5 mm at the distal region 202. In other alternative embodiments, the outer diameter decreases while the inner diameter increases, such that the wall tapers from both the inside and the outside.

In some embodiments, the elongate member 102, and therefore the medical device 100, are curved or bent, as shown in FIGS. 11A-11C. As used herein, the terms 'curved' or 'bent' refer to any region of non-linearity, or any deviation from a longitudinal axis of the device, regardless of the angle or length of the curve or bend. The medical device 100 includes a substantially rectilinear section 302 and a curved section 300 extending from the substantially rectilinear section 302. Typically, the curved section 300 is located in the distal region 202 of the elongate member 102, and may occur over various lengths and at various angles. In some examples, curved section 300 has a relatively large radius, for example, between about 10 cm and about 25 cm, and traverses a small portion of a circumference of a circle, for example between about 20 and about 40 degrees, as shown in FIG. 11B. In alternative examples, the curved section 300 has a relatively small radius, for example, between about 4 cm and about 7 cm, and traverses a substantially large portion of a circumference of a circle, for example, between about 50 and about 110 degrees, as shown in FIG. 11C. In one specific embodiment, the curved section 300 begins about 8.5 cm from the distal end 206 of the elongate member 102, has a radius of about 6 cm, and traverses about 80 degrees of a circumference of a circle. In an alternative embodiment, the curved section has a radius of about 5.4 cm and traverses about 50 degrees of a circumference of a circle. In a further embodiment, the curved section has a radius of about 5.7 cm and traverses about 86 degrees of a circumference of a circle. This configuration helps in positioning the elongate member 102 such that the distal end 206 is substantially perpendicular to the tissue through which the channel is to be created. This perpendicular positioning transmits the most energy when a user exerts a force through the elongate member 102, which provides enhanced feedback to the user.

The curved section 300 may be applied to the elongate member 102 by a variety of methods. For example, in one embodiment, the elongate member 102 is manufactured in a curved mold. In another embodiment, the elongate member 102 is manufactured in a substantially straight shape then placed in a heated mold to force the elongate member 102 to adopt a curved shape. Alternatively, the elongate member 102 is manufactured in a substantially straight shape and is forcibly bent by gripping the elongate member 102 just proximal to the region to be curved and applying force to curve the distal region 202. In an alternative embodiment, the elongate member 102 includes a main member 210 and an end member 212, as described with respect to FIG. 10D, which are joined together at an angle (not shown in the drawings). That is, rather than being coaxial, the main member 210 and an end member 212 are joined such that, for example, they are at an angle of 45° with respect to each other.

As mentioned herein above, in some embodiments the proximal region 200 of the elongate member 102 is structured to be coupled to an energy source. To facilitate this coupling, the proximal region 200 may comprise a hub 108 that allows for the energy source to be electrically connected to the elongate member 102. Further details regarding the hub 108 are described herein below. In other embodiments, the proximal region 200 is coupled to an energy source by other methods known to those of skill in the art, and the invention is not limited in this regard.

In typical embodiments, the elongate member 102 is made from an electrically conductive material that is biocompatible. As used herein, 'biocompatible' refers to a material that is suitable for use within the body during the course of a surgical procedure. Such materials include stainless steels, copper, titanium and nickel-titanium alloys (for example, NITINOL®), amongst others. Furthermore, in some embodiments, different regions of the elongate member 102 are made from different materials. In an example of the embodiment of FIG. 10D, the main member 210 is made from stainless steel such that it provides column strength to a portion of the elongate member 102 (for example, the force transmitting portion), and the end member 212 is made out of a nickel-titanium alloy such as NITINOL®, such that it provides flexibility to a portion of the elongate member 102 (for example, the distal portion). Embodiments wherein the force transmitting portion of the elongate member 102 is manufactured from stainless steel often result in medical device 100 having a similar amount of column strength to a device of the prior art, for example, a mechanical perforator such as a Brockenbrough™ needle. This is beneficial in that it provides a familiar 'feel' to users familiar with such devices. In some embodiments comprising a curved or bent elongate member 102, the rectilinear section 302 is made from stainless steel such that it provides column strength to the elongate member 102, and the curved section 300 is made out of a nickel-titanium alloy such as NITINOL®, such that it provides flexibility to the elongate member 102. In addition, the use of NITINOL® for curved section 300 is advantageous as the superelastic properties of this material helps in restoring the shape of the curved section 300 after the curved section 300 is straightened out, for example, when placed within a dilator.

As mentioned herein above, an electrical insulation 104 is disposed on at least a portion of the outer surface of the elongate member 102. In some embodiments, for example as shown in FIG. 1, electrical insulation 104 covers the circumference of the elongate member 102 from the proximal region 200 of the elongate member 102 to the distal region 202 of the elongate member 102. In other words, the force transmitting portion 114 and distal portion 112 are electrically conductive, and the electrical insulation substantially covers the force transmitting portion 114 and distal portion 112, while the electrode 106 remains substantially uninsulated. When a source of energy is coupled to the proximal region 200 of the elongate member 102, the electrical insulation 104 substantially prevents leakage of energy along the length of the elongate member 102, thus allowing energy to be delivered from the proximal region 200 of the elongate member 102 to the electrode 106.

Figure 3A:
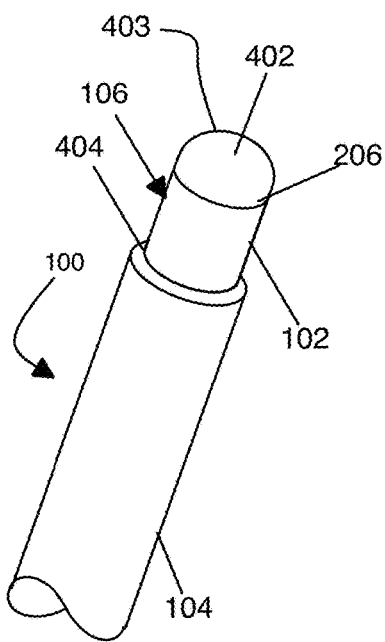
FIGS. 3A to 3D illustrate perspective views of various electrode configurations.
Figure 3B:
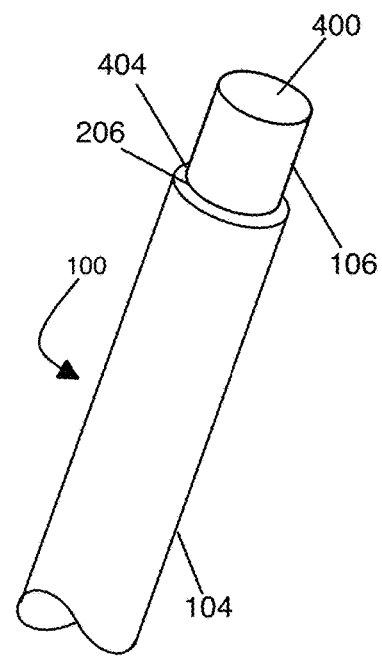
Figure 3C:
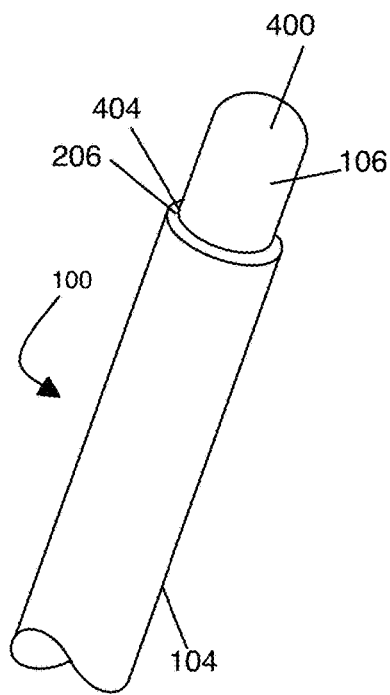

In embodiments as illustrated in FIG. 1, the electrical insulation 104 may extend to different locations on the distal region 202 (FIG. 10), depending on the configuration of the electrode 106. Typically, electrical insulation 104 extends to a proximal end 404 of the electrode 106, which may or may not coincide with the distal end of the elongate member 102. For example, as shown in FIG. 3A, the distal-most 1.5 mm of the elongate member 102 serves as at least a portion of the electrode 106. In these embodiments, electrical insulation 104 extends to a point about 1.5 mm proximal to the distal end 206 of the elongate member 102. In the embodiments of FIGS. 3B-3C, an external component 400 coupled to the distal end of the elongate member 102 serves as the electrode 106. In such embodiments, the proximal end 404 of the electrode 106 substantially coincides with the distal end 206 of the elongate member 102, and thus the electrical insulation 104 extends to the distal end 206 of the elongate member 102. In some embodiments, the electrical insulation 104 extends beyond the distal end 206 of the elongate member 102, and covers a portion of the external component 400. This typically aids in securing the external component 400 to the elongate member 102. The uncovered portion of the external component 400 can then serve as the electrode 106. In other embodiments, for example as shown in FIG. 3A, the distal-most portion of the elongate member 102, as well as a rounded external component 402, serve as the electrode 106. In this embodiment, the electrical insulation 104 extends to a point substantially adjacent to the distal end 206 of the elongate member 102. In one example, the electrical insulation 104 extends to a point about 1.0 mm away from the distal end 206 of the elongate member 102.

The electrical insulation 104 may be one of many biocompatible dielectric materials, including but not limited to, polytetrafluoroethylene (PTFE, Teflon®), parylene, polyimides, polyethylene terepthalate (PET), polyether block amide (PEBAX®), and polyetheretherketone (PEEK™), as well as combinations thereof. The thickness of the electrical insulation 104 may vary depending on the material used. Typically, the thickness of the electrical insulation 104 is from about 0.02 mm to about 0.12 mm.

In some embodiments, the electrical insulation 104 comprises a plurality of dielectric materials. This is useful, for example, in cases where different properties are required for different portions of the electrical insulation 104. In certain applications, for example, substantial heat is generated at the electrode 106. In such applications, a material with a sufficiently high melting point is required for the distal-most portion of the electrical insulation 104, so that this portion of the electrical insulation 104, located adjacent to electrode 106, doesn't melt. Furthermore, in some embodiments, a material with a high dielectric strength is desired for all of, or a portion of, the electrical insulation 104. In some particular embodiments, electrical insulation 104 has a combination of both of the aforementioned features.

With reference now to FIG. 2E, the electrical insulation 104 includes a first electrically insulating layer 218 made out of a first electrically insulating material, and a second electrically insulating layer 220 made out of a second electrically insulating material, and being substantially thinner than the first electrically insulating layer 218. The first electrically insulating layer 218 substantially covers the main member 210 substantially adjacent the end member 212, and the second electrically insulating layer 220 substantially covers the end member 212, with the electrode 106 substantially deprived from the second electrically insulating layer 220. In the illustrated embodiment, the first electrically insulating layer 218 overlaps the second electrically insulating layer 220 about the region of the taper of the elongate member 102. This configuration provides desirable mechanical properties for the medical device 100, as thinner materials are typically less rigid than thicker materials. Also, in some embodiments of the invention, the first electrically insulating layer 218 overlaps a portion of the second electrically insulating layer 220. However, in alternative embodiments of the invention, the electrical insulation 104 has any other suitable configuration, for example, the first electrically insulating layer 218 and the second electrically insulating layer 220 being made of the same material.

Figure 3D:
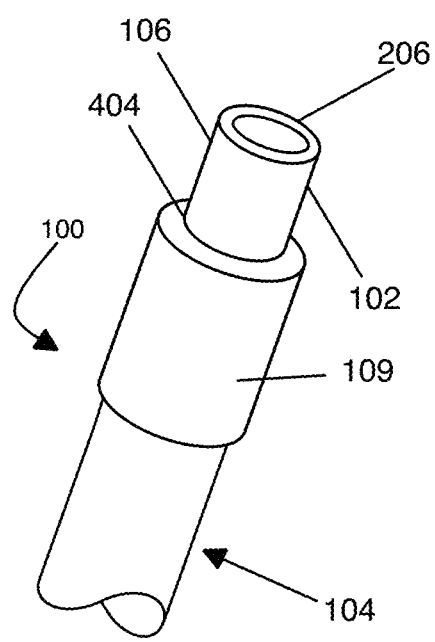

In further embodiments as shown in FIG. 3D, a heat shield 109 may be applied to the medical device 100 substantially adjacent to the electrode 106, for example, in order to prevent a distal portion of the electrical insulation 104 from melting due to heat generated by the electrode 106. For example, in some such embodiments, a thermally insulating material, for example Zirconium Oxide or polytetrafluoroethylene (PTFE), is applied over approximately the distalmost 2 cm of the electrical insulation 104. Typically, the heat shield 109 protrudes substantially radially outwardly from the remainder of the distal portion 112 and substantially longitudinally from the electrode 106 in a direction leading towards the handle 110.

The electrical insulation 104 may be applied to the elongate member 102 by a variety of methods. For example, if the electrical insulation 104 includes PTFE, it may be provided in the form of heat-shrink tubing, which is placed over the elongate member 102 and subjected to heat to substantially tighten around the elongate member 102. If the electrically insulating material is parylene, for example, it may be applied to the elongate member 102 by vapor deposition. In other embodiments, depending on the specific material used, the electrical insulation 104 may be applied to the elongate member 102 using alternate methods such as dip-coating, co-extrusion, or spraying.

As mentioned herein above, in embodiments of the present invention the elongate member 102 comprises an electrode 106 at the distal region, the electrode 106 configured to create a channel via radiofrequency perforation. As used herein, 'radiofrequency perforation' refers to a procedure in which radiofrequency (RF) electrical energy is applied from a device to a tissue to create a perforation or fenestration through the tissue. Without being limited to a particular theory of operation, it is believed that the RF energy serves to rapidly increase tissue temperature to the extent that water in the intracellular fluid converts to steam, inducing cell lysis as a result of elevated pressure within the cell. Furthermore, electrical breakdown may occur within the cell, wherein the electric field induced by the alternating current exceeds the dielectric strength of the medium located between the radiofrequency perforator and the cell, causing a dielectric breakdown. In addition, mechanical breakdown may occur, wherein alternating current induces stresses on polar molecules in the cell. Upon the occurrence of cell lysis and rupture, a void is created, allowing the device to advance into the tissue with little resistance. In order to increase the current density delivered to the tissue and achieve this effect, the device from which energy is applied, i.e. the electrode, is relatively small, having an electrically exposed surface area of no greater than about 15 $mm^2$. In addition, the energy source is capable of applying a high voltage through a high impedance load, as will be discussed further herein below. This is in contrast to RF ablation, whereby a larger-tipped device is utilized to deliver RF energy to a larger region in order to slowly desiccate the tissue. As opposed to RF perforation, which creates a void in the tissue through which the device is advanced, the objective of RF ablation is to create a large, non-penetrating lesion in the tissue, in order to disrupt electrical conduction. Thus, for the purposes of the present invention, the electrode refers to a device which is electrically conductive and exposed, having an exposed surface area of no greater than about 15 $mm^2$, and which is operable to delivery energy to create a perforation or fenestration through tissue when coupled to a suitable energy source and positioned at a target site. The perforation is created, for example, by vaporizing intracellular fluid of cells with which it is in contact, such that a void, hole, or channel is created in the tissue located at the target site.

In further embodiments, as shown in FIG. 3A, it is desirable for the distal end 206 of the elongate member 102 to be closed. For example, in some embodiments, it is desirable for fluids to be injected radially from the elongate member 102, for example, through side-ports in elongate member 102 substantially without being injected distally from the elongate member 102, as discussed herein below. In these embodiments, a closed distal end 206 facilitates radial injection of fluid while preventing distal injection.

It is a common belief that it is necessary to have a distal opening in order to properly deliver a contrast agent to a target site. However, it was unpredictably found that it is possible to properly operate the medical device 100 in the absence of distal openings. Advantageously, these embodiments reduce the risk that a core of tissue becomes stuck in such a distal opening when creating the channel through the tissue. Avoiding such tissue cores is desirable as they may enter the blood circulation, which creates risks of blocking blood vessels, leading to potentially lethal infarctions.

Thus, as shown in FIG. 3A, a rounded external component 402, for example an electrode tip, is operatively coupled to the distal end 206. In this embodiment, the exposed portion of the distal region 202 (FIG. 10A to 10D), as well as the rounded external component 402, serves as the electrode 106. In such an embodiment, if the outer diameter of the elongate member 102 is 0.7 mm, the rounded external component 402 is a hemisphere having a radius of about 0.35 mm, and the length of the distal-most exposed portion of the elongate member 102 is about 2.0 mm, and then the surface area of the electrode 106 is about 5.2 $mm^2$. Alternatively, as shown for example in FIG. 2E, the distal end of end member 212 is closed and used as the electrode 106, rather than a separate external component, In other embodiments as shown, for example, in FIGS. 3B and 3C, an electrically conductive and exposed external component 400 is electrically coupled to the distal end of the elongate member 102, such that the external component 400 serves as the electrode 106. In such embodiments, external component 400 is a cylinder having a diameter of between about 0.4 mm and about 1 mm, and a length of about 2 mm. Electrode 106 thus has an exposed surface area of between about 2.6 $mm^2$ and about 7.1 $mm^2$.

The external component 400 may take a variety of shapes, for example, cylindrical, main, conical, or truncated conical. The distal end of the external component 400 may also have different configuration, for example, rounded, or flat. Furthermore, some embodiments of the external component 400 are made from biocompatible electrically conductive materials, for example, stainless steel. The external component 400 may be coupled to the elongate member 102 by a variety of methods. In one embodiment, external component 400 is welded to the elongate member 102. In another embodiment, external component 400 is soldered to the elongate member 102. In one such embodiment, the solder material itself comprises the external component 400, e.g., an amount of solder is electrically coupled to the elongate member 102 in order to function as at least a portion of the electrode 106. In further embodiments, other methods of coupling the external component 400 to the elongate member 102 are used, and the invention is not limited in this regard.

In these embodiments, as described herein above, the electrically exposed and conductive surface area of the electrode 106 is no greater than about 15 $mm^2$. In embodiments wherein the electrical insulation 104 covers a portion of the external component 400, the portion of the external component 400 that is covered by the electrical insulation 104 is not included when determining the surface area of the electrode 106.

Referring again to FIG. 3A, in some embodiments, the distal portion 112 defines a distal tip 403, the distal tip 403 being substantially atraumatic. In other words, the distal end of the medical device 100 is structured such that it is substantially atraumatic, or blunt. As used herein, the terms 'atraumatic' and 'blunt' refer to a structure that is not sharp, and includes structures that are rounded, obtuse, or flat, amongst others, as shown, for example, in FIG. 3A. In embodiments wherein the distal end of the medical device 100 is substantially blunt, the blunt distal end is beneficial for avoiding unwanted damage to non-target areas within the body. That is, if mechanical force is unintentionally applied to the medical device 100 when the distal end of the medical device 100 is located at a non-target tissue, the medical device 100 is less likely to perforate the non-target tissue.

In some embodiments, the distal tip 403 is substantially bullet-shaped, as shown in FIG. 2E, which allows the intended user to drag the distal tip 403 across the surface of tissues in the patient's body and to catch on to tissues at the target site. For example, if the target site includes a fossa ovalis, as described further herein below, the bullet-shaped tip may catch on to the fossa ovalis so that longitudinal force applied at a proximal portion of medical device 100 causes the electrode 106 to advance into and through the fossa ovalis rather than slipping out of the fossa ovalis. Because of the tactile feedback provided by the medical device 100, this operation facilitates positioning of the medical device 100 prior to energy delivery to create a channel.

As mentioned herein above, in some embodiments, the medical device 100 comprises a hub 108 coupled to the proximal region. In some embodiments, the hub 108 is part of the handle 110 of the medical device 100, and facilitates the connection of the elongate member 102 to an energy source and a fluid source, for example, a contrast fluid source.

Figure 12A:
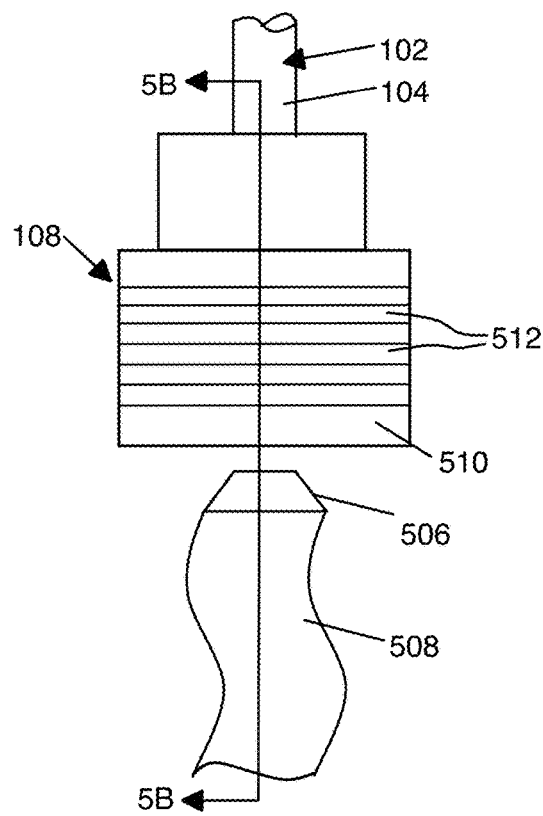
FIG. 12A illustrates a top elevation view of an embodiment of a hub.
Figure 12B:
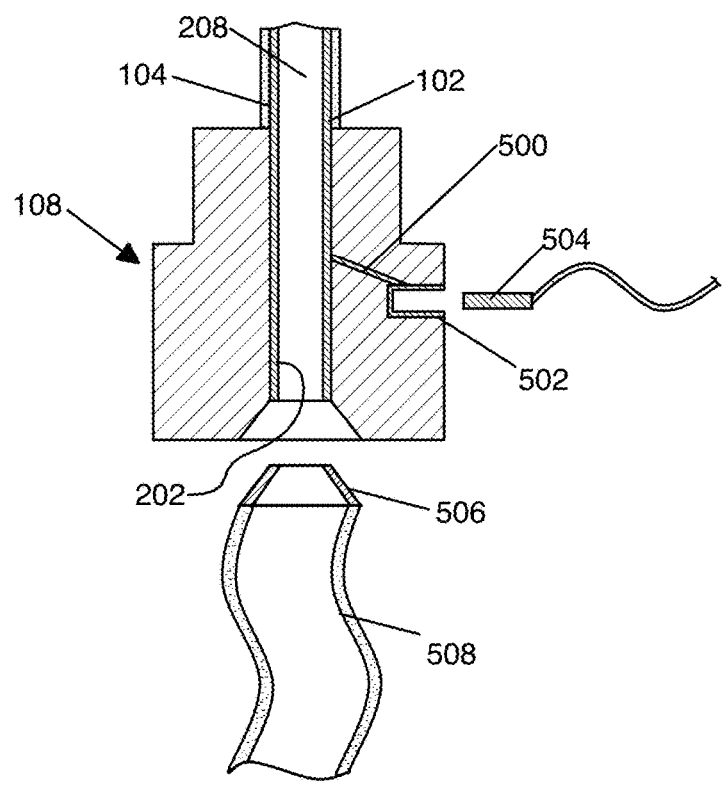
FIG. 12B illustrates a side cross-sectional view taken along the line 5B-5B of FIG. 12A.

In the embodiment illustrated in FIGS. 12A and 12B, the proximal region 200 the of the elongate member 102 is electrically coupled to the hub 108, which is structured to electrically couple the elongate member 102 to a source of energy, for example, a radiofrequency generator. In one embodiment, the hub 108 comprises a conductive wire 500 that is connected at one end to the elongate member 102, for example, by welding or brazing. The other end of the wire 500 is coupled to a connector (i.e. a connector means for receiving), for example a banana jack 502, that can be electrically coupled to a banana plug 504, which is electrically coupled to a source of energy. Thus, electrical energy may be delivered from the energy source, through plug 504, jack 502, and wire 500 to the elongate member 102 and electrode 106. In other embodiments, other hubs or connectors that allow elongate member 102 to be connected to a source of fluid and a source of energy are used, and the invention is not limited in this regard.

In some embodiments, medical device 100 is a transseptal puncturing device comprising an elongate member which is electrically conductive, an electrical connector in electrical communication with the elongate member, and an electrode at a distal end of the electrically conductive elongate member for delivering energy to tissue. A method of using the transseptal puncturing device comprises the steps of (1) connecting an electrically conductive component, which is in electrical communication with a source of energy, to the electrical connector, and (2) delivering electrical energy through the electrode to a tissue. The electrically conductive component may comprise a plug, such as plug 504, and a wire connected thereto. Some embodiments of the method further comprise a step (3) of disconnecting the electrically conductive component from the electrical connector. In such embodiments, the electrically conductive component is connected in a releasable manner.

In some embodiments, the hub 108 is structured to be operatively coupled to a fluid connector 506, for example a Luer lock, which is connected to tubing 508. Tubing 508 is structured to be operatively coupled at one end to an aspirating device, a source of fluid 712 (for example a syringe), or a pressure sensing device (for example a pressure transducer 708). The other end of tubing 508 may be operatively coupled to the fluid connector 506, such that tubing 508 and lumen 208 are in fluid communication with each other, thus allowing for a flow of fluid between an external device and the lumen 208. In embodiments in which a hub 108 is part of handle 110, fluid and/or electrical connections do not have to be made only with the hub 108 i.e. connections may be made with other parts of the handle 110, or with parts of medical device 100 other than the handle.

In some embodiments, the hub 108 further comprises one or more curve-direction or orientation indicators 510 that are located on one side of the hub 108 to indicate the direction of the curved section 300. The orientation indicator(s) 510 may comprise inks, etching, or other materials that enhance visualization or tactile sensation.

In some embodiments of the invention, the handle 110 includes a relatively large, graspable surface so that tactile feedback can be transmitted relatively efficiently, for example by transmitting vibrations. In some embodiments of the invention, the handle 110 includes ridges 512, for example, in the hub 108, which enhance this tactile feedback. The ridges 512 allow the intended user to fully grasp the handle 110 without holding the handle 110 tightly, which facilitates the transmission of this feedback.

In some embodiments of the invention, the medical device 100, as shown in FIG. 2E, defines a lumen peripheral surface 602 extending substantially peripherally relative to the end member lumen 216, the lumen peripheral surface 602 being substantially covered with a lumen electrically insulating material 604. This configuration prevents or reduces electrical losses from the lumen peripheral surface 602 to any electrically conductive fluid located within the lumen 208. However, in other embodiments of the invention, the lumen peripheral surface 602 is not substantially covered with the lumen electrically insulating material 604.

Also, in some embodiments of the invention that include the curved section 300, the curved section 300 defines a center of curvature (not shown in the drawings), and the side-port(s) 600 extend from the lumen 208 substantially towards the center of curvature. This configuration substantially prevents the edges of the side-port(s) 600 from catching onto tissues as the tissues are perforated. However, in alternative embodiments of the invention, the side-port(s) 600 extend in any other suitable orientation.

In some embodiments, one or more radiopaque markers 714 (as shown in FIG. 8) are associated with the medical device 100 to highlight the location of important landmarks on medical device 100. Such landmarks include the location where the elongate member 102 begins to taper, the location of the electrode 106, or the location of any side-port(s) 600. In some embodiments, the entire distal region 202 of the medical device 100 is radiopaque. This can be achieved by filling the electrical insulation 104, for example Pebax®, with a radiopaque filler, for example Bismuth.

In some embodiments, the shape of the medical device 100 may be modifiable. For example, in some applications, it is desired that medical device 100 be capable of changing between a straight configuration, for example as shown in FIG. 1, and a curved configuration, for example as shown in FIGS. 11A-11C. This may be accomplished by coupling a pull-wire to the medical device 100, such that the distal end of the pull-wire is operatively coupled to the distal region of the medical device 100. When a user applies force to the proximal end of the pull wire, either directly or through an actuating mechanism, the distal region 202 of the medical device 100 is forced to deflect in a particular direction. In other embodiments, other means for modifying the shape of the medical device 100 are used, and the invention is not limited in this regard.

In some embodiments, the medical device 100 includes at least one further electrically conductive component, located proximal to the electrode 106. For example, the electrically conductive component may be a metal ring positioned on or around the electrical insulation 104 which has a sufficiently large surface area to be operable as a return electrode. In such an embodiment, the medical device 100 may function in a bipolar manner, whereby electrical energy flows from the electrode 106, through tissue at the target site, to the at least one further electrically conductive component. Furthermore, in such embodiments, the medical device 100 includes at least one electrical conductor, for example a wire, for conducting electrical energy from the at least one further conductive component to a current sink, for example, circuit ground.

In some embodiments, medical device 100 is used in conjunction with a source of radiofrequency energy suitable for perforating material within a patient's body. The source of energy may be a radiofrequency (RF) electrical generator 700, operable in the range of about 100 kHz to about 1000 kHz, and designed to generate a high voltage over a short period of time. More specifically, in some embodiments, the voltage generated by the generator increases from about 0 V (peak-to-peak) to greater than about 75 V (peak-to-peak) in less than about 0.6 seconds. The maximum voltage generated by generator 700 may be between about 180V peak-to-peak and about 3000V peak-to-peak. The waveform generated may vary, and may include, for example, a sine-wave, a rectangular-wave, or a pulsed rectangular wave, amongst others. During delivery of radiofrequency energy, the impedance load may increase due to occurrences such as tissue lesioning near the target-site, or the formation of a vapor layer following cell rupture. In some embodiments, the generator 700 is operable to continue to increase the voltage, even as the impedance load increases. For example, energy may be delivered to a tissue within a body at a voltage that rapidly increases from about 0 V (RMS) to about 220 V (RMS) for a period of between about 0.5 seconds and about 5 seconds.

Without being limited to a particular theory of operation, it is believed that under particular circumstances, as mentioned herein above, dielectric breakdown and arcing occur upon the delivery of radiofrequency energy, whereby polar molecules are pulled apart. The combination of these factors may result in the creation of an insulative vapor layer around the electrode, therein resulting in an increase in impedance, for example, the impedance may increase to greater than 400052. In some embodiments, despite this high impedance, the voltage continues to increase. Further increasing the voltage increases the intensity of fulguration, which may be desirable as it allows for an increased perforation rate. An example of an appropriate generator for this application is the BMC RF Perforation Generator (model number RFP-100, Baylis Medical Company, Montreal, Canada). This generator delivers continuous RF energy at about 460 kHz.

In some embodiments, a dispersive electrode or grounding pad 702 is electrically coupled to the generator 700 for contacting or attaching to a patient's body to provide a return path for the RF energy when the generator 700 is operated in a monopolar mode. Alternatively, in embodiments utilizing a bipolar device, as described hereinabove, a grounding pad is not necessary as a return path for the RF energy is provided by the further conductive component.

In the embodiment illustrated in FIGS. 12A and 12B, the medical device 100 is operatively coupled to the tubing 508 using fluid connector 506 located at the proximal end of the medical device 100. In some embodiments, the tubing 508 is made of a polymeric material such as polyvinylchloride (PVC), or another flexible polymer. Some embodiments include the tubing 508 being operatively coupled to an adapter 704. The adapter is structured to provide a flexible region for the user to handle when releasably coupling an external pressure transducer, a fluid source, or other devices to the adapter. In some embodiments, couplings between elongate member 102, fluid connector 506, and tubing 508, and between tubing 508 and adapter 704, are temporary couplings such as Luer locks or other releasable components. In alternative embodiments, the couplings are substantially permanent, for example a bonding agent such as a UV curable adhesive, an epoxy, or another type of bonding agent. Some embodiments of the medical device 100 include a distal aperture in fluid communication with the lumen 208 wherein the distal aperture is a side-port 600, while some alternative embodiments have a distal aperture defined by an open distal end.

In one broad aspect, the electrosurgical medical device 100 is usable to deliver energy to a target site within a patient's body to perforate or create a void or channel in a material at the target site. Further details regarding delivery of energy to a target site within the body may be found in U.S. patent application Ser. No. 13/113,326 (filed on May 23, 2011), Ser. No. 10/347,366 (filed on Jan. 21, 2003, now U.S. Pat. No. 7,112,197), Ser. No. 10/760,749 (filed on Jan. 21, 2004), Ser. No. 10/666,288 (filed on Sep. 19, 2003), and Ser. No. 11/265,304 (filed on Nov. 3, 2005), and U.S. Pat. No. 7,048,733 (application Ser. No. 10/666,301, filed on Sep. 19, 2003) and U.S. Pat. No. 6,565,562 (issued on May 20, 2003), all of which are incorporated herein by reference.

In one specific embodiment, the target site comprises a tissue within the heart of a patient, for example, the atrial septum of the heart. In such an embodiment, the target site may be accessed via the inferior vena cava (IVC), for example, through the femoral vein.

In one such embodiment, an intended user introduces a guidewire into a femoral vein, typically the right femoral vein, and advances it towards the heart. A guiding sheath, for example, a sheath as described in U.S. patent application Ser. No. 10/666,288 (filed on Sep. 19, 2003), previously incorporated herein by reference, is then introduced into the femoral vein over the guidewire, and advanced towards the heart. The distal ends of the guidewire and sheath are then positioned in the superior vena cava. These steps may be performed with the aid of fluoroscopic imaging. When the sheath is in position, a dilator, for example the TorFlex™ Transseptal Dilator of Baylis Medical Company Inc. (Montreal, Canada), or the dilator as described in U.S. patent application Ser. No. 11/727,382 (filed on Mar. 26, 2007), incorporated herein by reference, is introduced into the sheath and over the guidewire, and advanced through the sheath into the superior vena cava. The sheath aids in preventing the dilator from damaging or puncturing vessel walls, for example, in embodiments comprising a substantially stiff dilator. Alternatively, the dilator may be fully inserted into the sheath prior to entering the body, and both may be advanced simultaneously towards the heart. When the guidewire, sheath, and dilator have been positioned in the superior vena cava, the guidewire is removed from the body, and the sheath and dilator are retracted slightly such that they enter the right atrium of the heart. An electrosurgical device, for example medical device 100 described herein above, is then introduced into the lumen of the dilator, and advanced toward the heart.

In this embodiment, after inserting the electrosurgical device into the dilator, the user positions the distal end of the dilator against the atrial septum. The electrosurgical device is then positioned such that electrode 106 is aligned with or protruding slightly from the distal end of the dilator. When the electrosurgical device and the dilator have been properly positioned, for example, against the fossa ovalis of the atrial septum, a variety of additional steps may be performed. These steps may include measuring one or more properties of the target site, for example, an electrogram or ECG (electrocardiogram) tracing and/or a pressure measurement, or delivering material to the target site, for example, delivering a contrast agent through side-port(s) 600 and/or open distal end 206. Such steps may facilitate the localization of the electrode 106 at the desired target site. In addition, as mentioned herein above, the tactile feedback provided by the proposed medical device 100 is usable to facilitate positioning of the electrode 106 at the desired target site.

With the electrosurgical device and the dilator positioned at the target site, energy is delivered from the energy source, through medical device 100, to the target site. For example, energy is delivered through the elongate member 102, to the electrode 106, and into the tissue at the target site. In some embodiments, the energy is delivered at a power of at least about 5 W at a voltage of at least about 75 V (peak-to-peak), and, as described herein above, functions to vaporize cells in the vicinity of the electrode, thereby creating a void or perforation through the tissue at the target site. If the heart was approached via the inferior vena cava, as described herein above, the user applies force in the substantially cranial direction to the handle 110 of the electrosurgical device as energy is being delivered. The force is then transmitted from the handle to the distal portion 112 of the medical device 100, such that the distal portion 112 advances at least partially through the perforation. In these embodiments, when the distal portion 112 has passed through the target tissue, that is, when it has reached the left atrium, energy delivery is stopped. In some embodiments, the step of delivering energy occurs over a period of between about 1 s and about 5 s.

At this point in the procedure, the diameter of the perforation is typically substantially similar to the outer diameter of the distal portion 112. In some examples, the user may wish to enlarge the perforation, such that other devices such as ablation catheters or other surgical devices are able to pass through the perforation. Typically, to do this, the user applies force to the proximal region of the dilator, for example, in the cranial direction if the heart was approached via the inferior vena cava. The force typically causes the distal end of the dilator to enter the perforation and pass through the atrial septum. The electrosurgical device is operable to aid in guiding the dilator through the perforation, by acting as a substantially stiff rail for the dilator. In such embodiments, a curve, for example, curved section 300 of the medical device 100, typically assists in anchoring the electrosurgical device in the left atrium. In typical embodiments, as force is applied, portions of the dilator of larger diameter pass through the perforation, thereby dilating, expanding, or enlarging the perforation. In some embodiments, the user also applies torque to aid in maneuvering the dilator. Alternatively, in embodiments wherein the device is tapered, the device may be advanced further into the left atrium, such that larger portions of the device enter and dilate the perforation.

In some embodiments, when the perforation has been dilated to a suitable size, the user stops advancing the dilator. A guiding sheath is then advanced over the dilator through the perforation. In alternative embodiments, the sheath is advanced simultaneously with the dilator. At this point in the procedure, the user may retract the dilator and the electrosurgical device proximally through the sheath, leaving only the sheath in place in the heart. The user is then able to perform a surgical procedure on the left side of the heart via the sheath, for example, introducing a surgical device into the femoral vein through the sheath for performing a surgical procedure to treat electrical or morphological abnormalities within the left side of the heart.

If an apparatus of the present invention, as described herein above, is used to carry out a procedure as described herein, then the user is able to maintain the 'feel' of a mechanical perforator, for example a Brockenbrough™ needle, without requiring a sharp tip and large amounts of mechanical force to perforate the atrial septum. Rather, a radiofrequency perforator, for example, the electrode 106, is used to create a void or channel through the atrial septum, as described herein above, while reducing the risk of accidental puncture of non-target tissues.

In other embodiments, methods of the present invention may be used for treatment procedures involving other regions within the body, and the invention is not limited in this regard. For example, rather than the atrial septum, embodiments of devices, systems, and methods of the present invention can be used to treat pulmonary atresia. In some such embodiments, a sheath is introduced into the vascular system of a patient and guided to the heart, as described herein above. A dilator is then introduced into the sheath, and advanced towards the heart, where it is positioned against the pulmonary valve. An electrosurgical device comprising an electrode is then introduced into the proximal region of the dilator, and advanced such that it is also positioned against the pulmonary valve. Energy is then delivered from the energy source, through the electrode of the electrosurgical device, to the pulmonary valve, such that a puncture or void is created as described herein above. When the electrosurgical device has passed through the valve, the user is able to apply a force to the proximal region of the dilator, for example, in a substantially cranial direction. The force can be transmitted to the distal region of the dilator such that the distal region of the dilator enters the puncture and advances through the pulmonary valve. As regions of the dilator of larger diameter pass through the puncture, the puncture or channel becomes dilated.

In other applications, embodiments of a device of the present invention can be used to create voids or channels within or through other tissues of the body, for example within or through the myocardium of the heart. In other embodiments, the device is used to create a channel through a fully or partially occluded lumen within the body. Examples of such lumens include, but are not limited to, blood vessels, the bile duct, airways of the respiratory tract, and vessels and/or tubes of the digestive system, the urinary tract and/or the reproductive system. In such embodiments, the device is typically positioned such that an electrode of the device is substantially adjacent the material to be perforated. Energy is then delivered from an energy source, through the electrode 106, to the target site such that a void, puncture, or channel is created in or through the tissue.

This disclosure describes embodiments of a kit and its constituent components which together form an apparatus in which fluid communication between a medical device's lumen and the surrounding environment is provided by a conduit cooperatively defined by the medical device and a tubular member into which the device is inserted. The medical device and tubular member are configured to fit together such that an outer surface of the distal region of the medical device cooperates with an inner surface of the tubular member to define the conduit between the side-port of the medical device and a distal end of the tubular member. The conduit is operable for a variety of applications including injecting fluid, withdrawing fluid, and measuring pressure. Methods of assembling and using the apparatus are described as well.

This disclosure further describes an electrosurgical device configured for force transmission from a distal portion of the electrosurgical device to a proximal portion of the electrosurgical device to thereby provide tactile feedback to a user. The proximal portion of the device comprises a handle and/or a hub, with the handle (or hub) including an electrical connector (i.e. a connector means) which is configured to receive, in a releasable manner, an electrically conductive component which is operable to be in electrical communication with an energy source to allow the user to puncture a tissue layer. In some cases, a radiofrequency (RF) energy source is used to selectively apply RF energy to the tissue. Typical embodiments of the device include insulation to protect the user and the patient.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations are apparent to those skilled in the art. Accordingly, it is intended to embrace all such alternatives, modifications, and variations that fall within the scope of the appended claims.

What is claimed is:

1. A connector system for connecting a source of energy and a source of fluid to an electrosurgical device comprising an electrically conductive elongate member and defining a proximal portion and a distal portion, the connector system comprising a hub comprising:
    an electrically conductive lengthwise member having a lengthwise member distal region and a lengthwise member proximal region, wherein the lengthwise member defines a hub lumen therebetween for providing a conduit for flow of a fluid, said lengthwise member configured to be operatively coupled to the electrosurgical device,
    a hub fluid connector associated with the lengthwise member for operatively connecting the lengthwise member to a fluid source, and
    a hub electrical connector associated with the lengthwise member for electrically coupling the lengthwise member to an energy source,
    whereby, in use, an electrical conduction pathway between the energy source and the electrosurgical device includes the lengthwise member, and whereby the lengthwise member provides a fluid pathway conduit between the fluid source and the electrosurgical device.

2. The connector system according to claim 1 wherein the hub is configured to be removable from the electrosurgical device, thereby allowing other devices to be slid over the electrosurgical device.

3. The connector system of claim 2 wherein the hub is coupled (locked) to the electrosurgical device using a coupling mechanism for preventing undesired disengagement and/or rotation of the hub from the electrosurgical device.

4. The connector system according to claim 1 wherein the hub is configured to be rotatable with respect to the electrosurgical device while maintaining electrical and fluid communication with the electrosurgical device.

5. The connector system of claim 4 wherein the hub is coupled (locked) to the electrosurgical device using a coupling mechanism for preventing undesired disengagement and/or rotation of the hub from the electrosurgical device.

6. The connector system of claim 1 wherein the lengthwise member has an inner wall and said inner wall is fitted with an electrically insulative material in order to prevent energy from being conducted from the lengthwise member to the fluid within the hub lumen defined by the lengthwise member.

7. The connector system of claim 6, wherein the electrical connector comprises a jack for receiving the electrically conductive component.

8. The connector system according to claim 6, wherein the hub comprises ridges for enhancing a tactile feedback.

9. The connector system according to claim 8, wherein the electrosurgical device further comprises a distal tip including an electrode for delivering energy to a tissue and the electrically conductive elongate member defines a lumen.

10. A connector system for connecting a source of energy and a source of fluid to an electrosurgical device comprising an electrically conductive elongate member and defining a proximal portion and a distal portion, said connector system comprising a hub, the hub comprising:
    a hub lumen defined therethrough from proximal end to distal end of the hub for receiving the electrosurgical device and for providing a pathway for flow of a fluid, said hub lumen configured to be operatively coupled to the electrosurgical device and for transporting electrical conductors or fluids,
    a hub fluid connector associated with the hub for operatively connecting to a fluid source and,
    a hub electrical connector associated with the hub for electrically coupling the hub to an energy source.

11. The connector system of claim 10 wherein the lengthwise member has an inner wall and said inner wall is fitted with an electrically insulative material in order to prevent energy from being conducted from the lengthwise member to the fluid within the hub lumen defined by the lengthwise member.

12. The connector system of claim 11, wherein the electrical connector comprises a jack for receiving the electrically conductive component.

13. The connector system according to claim 12, wherein the electrosurgical device further comprises a distal tip including an electrode for delivering energy to a tissue and the electrically conductive elongate member defines a lumen.

14. A connector system for connecting a source of energy and a source of fluid to an electrosurgical device, the connector system comprising a hub, the hub comprising:
    a hub lumen defined therethrough from a hub proximal end to hub distal end for providing a conduit for flow of a fluid, said hub lumen configured to be operatively coupled to an electrosurgical device,
    a hub fluid connector associated with hub for operatively connecting to a fluid source,
    a hub electrical receptacle configured to receive, in a releasable manner, an electrically conductive component operable to be electrically coupled to an energy source,
    whereby
    the hub provides an electrical conduction pathway between the energy source and the electrosurgical device, and further provides a fluid conduit between a fluid source and the electrosurgical device.

15. The connector system of claim 14 wherein the lengthwise member has an inner wall and said inner wall is fitted with an electrically insulative material in order to prevent energy from being conducted from the lengthwise member to the fluid within the hub lumen defined by the lengthwise member.

16. The connector system of claim 15, wherein the electrical connector comprises a jack for receiving the electrically conductive component.

17. An electrosurgical device comprising:
an electrically conductive elongate member and defining a proximal portion and a distal portion,
a hub for connecting a source of energy and a source of fluid to the electrosurgical device, said hub being coupled to the to the elongate member, the hub comprising,
an electrically conductive lengthwise member having a lengthwise member distal region and a lengthwise member proximal region, said lengthwise member defining a hub lumen between the lengthwise member distal region and the lengthwise member proximal region for providing a conduit for flow of a fluid,
a hub fluid connector associated with the lengthwise member for operatively connecting the lengthwise member to a fluid source, and
a hub electrical connector associated with the lengthwise member for electrically coupling the lengthwise member to an energy source,
whereby
in use, an electrical conduction pathway between the energy source and the elongate member includes the lengthwise member, and whereby the lengthwise member provides a fluid conduit between the fluid source and the electrosurgical device.

18. The electrosurgical device of claim 17 wherein the lengthwise member has an inner wall and said inner wall is fitted with an electrically insulative material in order to prevent energy from being conducted from the lengthwise member to the fluid within the hub lumen defined by the lengthwise member.

19. The electrosurgical device of claim 18, wherein the electrical connector comprises a jack for receiving the electrically conductive component.

20. The connector system according to claim 19, wherein the electrosurgical device further comprises a distal tip including an electrode for delivering energy to a tissue and the electrically conductive elongate member defines a lumen.

* * * * *